US009085571B2

(12) United States Patent
Ghosh

(10) Patent No.: US 9,085,571 B2
(45) Date of Patent: Jul. 21, 2015

(54) NONPEPTIDE HIV-1 PROTEASE INHIBITORS

(71) Applicant: Purdue Research Foundation, West Lafayette, IN (US)

(72) Inventor: Arun K. Ghosh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/322,808

(22) Filed: Jul. 2, 2014

(65) Prior Publication Data

US 2014/0315946 A1    Oct. 23, 2014

Related U.S. Application Data

(62) Division of application No. 13/001,339, filed as application No. PCT/US2009/049407 on Jul. 1, 2009, now Pat. No. 8,791,135.

(60) Provisional application No. 61/077,343, filed on Jul. 1, 2008.

(51) Int. Cl.
| A61K 31/40 | (2006.01) |
| A61K 31/44 | (2006.01) |
| C07D 207/02 | (2006.01) |
| C07D 211/04 | (2006.01) |
| C07D 413/12 | (2006.01) |
| C07C 311/29 | (2006.01) |
| C07D 217/04 | (2006.01) |
| C07D 263/32 | (2006.01) |
| C07D 277/28 | (2006.01) |
| C07D 417/04 | (2006.01) |
| C07C 317/32 | (2006.01) |
| C07C 317/50 | (2006.01) |
| C07D 217/12 | (2006.01) |
| C07D 277/30 | (2006.01) |

(52) U.S. Cl.
CPC ............ *C07D 413/12* (2013.01); *C07C 311/29* (2013.01); *C07C 317/32* (2013.01); *C07C 317/50* (2013.01); *C07D 217/04* (2013.01); *C07D 217/12* (2013.01); *C07D 263/32* (2013.01); *C07D 277/28* (2013.01); *C07D 277/30* (2013.01); *C07D 417/04* (2013.01); *C07C 2101/14* (2013.01)

(58) Field of Classification Search
CPC .... C07D 207/02; C07D 211/04; A61K 31/40; A61K 31/44; A61K 31/165
USPC ........... 548/400; 514/315, 408, 619; 546/184; 564/163
See application file for complete search history.

(56) References Cited

U.S. PATENT DOCUMENTS

| 5,723,490 | A | 3/1998 | Tung |
| 5,728,718 | A | 3/1998 | Randad et al. |
| 5,856,353 | A | 1/1999 | Tung et al. |
| 6,046,190 | A | 4/2000 | Vazquez et al. |
| 6,313,345 | B1 | 11/2001 | Vazquez et al. |
| 6,649,651 | B1 | 11/2003 | Wigerinck et al. |
| 8,791,135 | B2 | 7/2014 | Ghosh |
| 2002/0198378 | A1 | 12/2002 | Vazquez et al. |
| 2004/0122000 | A1 | 6/2004 | Hale et al. |
| 2005/0159469 | A1 | 7/2005 | Randolph et al. |
| 2005/0214890 | A1 | 9/2005 | Tan et al. |
| 2006/0052615 | A1 | 3/2006 | Coburn et al. |
| 2006/0106256 | A1 | 5/2006 | John et al. |
| 2006/0293286 | A1 | 12/2006 | Erickson et al. |
| 2007/0032470 | A1 | 2/2007 | Wu et al. |
| 2007/0082883 | A1 | 4/2007 | Ghosh et al. |
| 2007/0117793 | A1 | 5/2007 | Ghosh et al. |
| 2008/0096942 | A1 | 4/2008 | Tenbrink et al. |
| 2008/0132552 | A1 | 6/2008 | Kleinman et al. |
| 2010/0113582 | A1 | 5/2010 | Ghosh et al. |
| 2011/0178123 | A1 | 7/2011 | Ghosh et al. |

FOREIGN PATENT DOCUMENTS

| EP | 0609625 A1 | 8/1994 | |
| EP | 2307345 A1 | 4/2011 | |
| WO | WO-96/22087 A1 | 7/1996 | |
| WO | WO-96/33187 A1 | 10/1996 | |
| WO | WO-99/67254 A2 | 12/1999 | |
| WO | WO-01/25240 A1 | 4/2001 | |
| WO | WO-2006110668 | * 4/2006 | ............ C07C 233/78 |
| WO | WO-2008/133734 A2 | 11/2008 | |
| WO | WO-2010/002994 A1 | 1/2010 | |
| WO | WO-2010/006050 A1 | 1/2010 | |

OTHER PUBLICATIONS

Kaldor, Stephen W., et al. "Isophthalic acid derivatives: amino acid surrogates for the inhibition of HIV-1 protease." Bioorclanic & Medicinal Chemistry Letters 5.7 (1995): 721-726.*
"U.S. Appl. No. 13/001,339, First Preliminary Amendment filed Dec. 23, 2010", 10 pgs.
"U.S. Appl. No. 13/001,339, Non Final Office Action mailed Aug. 15, 2013", 6 pgs.
"U.S. Appl. No. 13/001,339, Notice of Allowance mailed Mar. 14, 2014", 10 pgs.
"U.S. Appl. No. 13/001,339, Response filed Jul. 8, 2013 to Restriction Requirement mailed Mar. 6, 2013", 9 pgs.
"U.S. Appl. No. 13/001,339, Response filed Dec. 16, 2013 to Non Final Office Action mailed Aug. 15, 2013", 11 pgs.
"U.S. Appl. No. 13/001,339, Restriction Requirement mailed Mar. 6, 2013", 9 pgs.
"U.S. Appl. No. 13/001,339, Second Preliminary Amendment filed Jan. 28, 2011", 8 pgs.
"European Application Serial No. 09774444.5, Extended European Search Report mailed Apr. 2, 2012", 7 pgs.

(Continued)

*Primary Examiner* — Kamal Saeed
*Assistant Examiner* — Janet L Coppins
(74) *Attorney, Agent, or Firm* — Schwegman Lundberg & Woessner, P.A.

(57) ABSTRACT

Novel compounds and compositions for treating patients in need of relief from HIV, AIDS and AIDS-related diseases are described. Methods for treating HIV, AIDS, and AIDS-related diseases using the compounds described herein are also described.

11 Claims, No Drawings

(56) References Cited

OTHER PUBLICATIONS

"European Application Serial No. 09774444.5, Office Action mailed Mar. 12, 2013", 5 pgs.

"European Application Serial No. 09774444.5, Office Action mailed Mar. 20, 2014", 4 pgs.

"European Application Serial No. 09774444.5, Office Action mailed Oct. 4, 2013", 5 pgs.

"European Application Serial No. 09774444.5, Response filed Feb. 5, 2014 to Office Action mailed Oct. 4, 2013", 15 pgs.

"European Application Serial No. 09774444.5, Response filed Jul. 9, 2013 to Office Action mailed Mar. 12, 2013", 15 pgs.

"European Application Serial No. 09774444.5, Response filed Oct. 25, 2012 to Extended European Search Report mailed Apr. 2, 2012", 19 pgs.

"European Application Serial No. 09774444.5, Supplementary European Search Report mailed Mar. 23, 2012", 3 pgs.

"International Application Serial No. PCT/US2009/049407, International Preliminary Report on Patentability mailed Jan. 5, 2011", 9 pgs.

"International Application Serial No. PCT/US2009/049407, International Search Report mailed Sep. 23, 2009", 2 pgs.

"International Application Serial No. PCT/US2009/049407, Written Opinion mailed Sep. 23, 2009", 8 pgs.

"Statine-Derived Tetrapeptide Inhibitors of .beta.-secretase", *Expert Opinion on Therapeutic Patents*, (Jun. 1, 2001), 1047-1050.

Amano, et al., "A Novel Bis-Tetrahydrofuranylurethane-containing Nonpeptidic Protease Inhibitor (PI), GRL-98065, is Potent against Multiple-PI-Resistant Human Immunodeficiency Virus In Vitro", *Antimicrobial Agents and Chemotherapy*, vol. 51. No. 6, (2007), 2143-2155.

Ami, et al., "Synthesis of Novel Amino Acids, L-Bis-Tetrahydrofuranylglycines", *Tetrahedron Letters*, vol. 43, (2002), 2931-2934.

Babe, et al., "Synthetic "Interface" Peptides Alter Dimeric Assembly of the HIV 1 and 2 Proteases", *Protein Science*, vol. 1, No. 10, (1992), 1244-1253.

Bannwarth, et al., "Molecular Tongs Containing Amino Acid Mimetic Fragments: New Inhibitors of Wild-Type and Mutated HIV-1 Protease Dimerization", *J. Med. Chem.*, vol. 49, No. 15, (2006), 4657-4664.

Bastiaens, et al., "Imaging the Intracellular Trafficking and State of the AB5 Quaternary Structure of Cholera Toxin", *EMBO Journal*, vol. 15, No. 16, (1996), 4246-4253.

Bowman, et al., "Switching between Allosteric and Dimerization Inhibition of HIV-1 Protease", *Chemistry & Biology*, vol. 12, No. 4, (2005), 439-444.

Carr, et al., "Toxicity of antiretroviral therapy and implications for drug development", *Nature Reviews Drug Disc*, vol. 2, (2003), 624-634.

Chen, et al., "Syntheses of a New Cerebroside Isolated from *Typhonium giganteum* Engl.", *Chinese Journal of Chemistry*, vol. 21, (2003), 937-943.

Clementz, et al., "Deubiquitinating and Interferon Antagonism Activities of *Coronavirus* Papain-Like Proteases", *J. Virol.*, 84(9), (2010), 4619-4629.

Das, et al., "Prediction of Potency of Protease Inhibitors Using Free Energy Simulations with Polarizable Quantum Mechanics-Based Ligand Charges and a Hybrid Water Model", *J. Chem. Info. Model*, 49(12), (2009), 2851-2862.

Davis, et al., "Inhibition of HIV-1 Replication by a Peptide Dimerization Inhibitor of HIV-1 Protease", *Antiviral Research*, vol. 72, No. 2, (2006), 89-99.

De Clercq, "Strategies in the design of antiviral drugs", *Nature Reviews Drug Disc*, vol. 1, (2002), 13-25.

De Meyer, et al., "TMC114, a Novel Human Immunodeficiency Virus Type 1 Protease Inhibitor Active against Protease Inhibitor-Resistant Viruses, Including a Broad Range of Clinical Isolates", *Antimicrobial Agents and Chemotherapy*, vol. 49, No. 6, (2005), 2314-2321.

Fang, et al., "PCR-Mediated Recombination: A General Method Applied to Construct Chimeric Infectious Molecular Clones of Plasma-Derived HIV-1 RNA", *Nature Medicine*, vol. 5, No. 2, (1999), 239-242.

Firulli, et al., "Altered Twist1 and Hand2 Dimerization is Associated with Saethre-Chotzen Syndrome and Limb Abnormalities", *Nature Genetics*, vol. 37, No. 4, (2005), 373-381.

Friesner, et al., "Glide: a new approach for rapid, accurate docking and scoring. 1. Method and assessment of docking accuracy", *J. Med, Chem.*, vol. 47, (2004), 1739-1749.

Frutos, et al., "Disruption of the HIV-1 Protease Dimer Interface Peptides: Structural Studies Using NMR Spectroscopy Combined with [2-13C]~Trp Selective Labeling", *Peptide Science*, vol. 88, No. 2, (2007), 164-173.

Fumero, et al., "New patterns of HIV-1 resistance during HAART", *European Society of Clinical Microbiology and Infectious Diseases*, vol. 9, (2003), 1077-1084.

Gatanaga, et al., "Amino Acid Substitutions in Gag Protein and Non-Cleavage Sites are Indispensable for the Development of a High Multitude of HIV-1 Resistance Against Protease Inhibitors", *Journal of Biological Chemistry* vol. 277 No. 8, (2002), 5952-5961.

Gatanaga, H. et al., "Altered HIV-1 gag Protein Interactions with Cyclophilin A (CypA) on the Acquisitionof H219Qand H219P Substitutios in the CypA Binding Loop", *J. Bioi. Chem*, 281(2), (2006).

Ghosh, et al., "2,5-Anhydro Sugar Diacid and 2,5-Anhydro Sugar Diamine Based Cz-Symmetric Peptidomimetics as Potential HIV-1 Protease Inhibitors", *Tetrahedron Letters*, (2001), 10121-24.

Ghosh, et al., "3-Tetrahydrofuran and pyranyl Urethanes as High Affinity P2-Ligands for HIV-1 Protease Inhibitors", *J. Med. Chem*, 36, (1993), 292-294.

Ghosh, et al., "A Convenient Enzymatic Route to Optically Active 1-Aminoindan-2-ol: Versatile Ligands for HIV-1 Protease Inhibitors and Asymmetric Syntheses", *Synthesis*, (1997), 541-44.

Ghosh, et al., "A Stereoselective Anti-aldol Route to (3R,3aS,6aR)-Tetrahydro-2H-furo[2,3-b]furan-3-ol: A Key Ligand for a New Generation of HIV Protease Inhibitors", *Synthesis*, (2006), 3015-3019.

Ghosh, et al., "An Efficient Synthesis of Hydroxyethylene Dipeptide Isosteres: The Core Unit of Potent HIV-1 Protease Inhibitors", *J. Org. Chem*, 56(23), (1991), 6500-6503.

Ghosh, et al., "Antiviral Activity of UIC-PI, a Novel Inhibitor of the Human Immunodeficiency Virus Type 1 Protease", *Antiviral Research*, 54(1), (2002), 29-36.

Ghosh, et al., "Asymmetric Aldol Route to Hydroxyethylamine Isostere: Stereoselective Synthesis of the Core Unit of Saquinavir", *J. Org. Chem*, 62(17), (1997), 6080-6082.

Ghosh, et al., "Asymmetric dihydroxylation route to a dipeptide isostere of a protease inhibitor: enantioselective synthesis of the core unit of ritonavir", *Chem. Commun*, (1999), 1025-26.

Ghosh, et al., "Bis-Tetrahydrofuran: A Privileged Ligand for Darunavi and a New Generation of HIV-Protease Inhibitors That Combat Drug-Resistance. Bis-Tetrahydrofuran", *ChemMedChem*, (2006), 939-950.

Ghosh, et al., "Chiral Auxiliary Mediated Conjugate reduction and Asymmetric Protonation: Synthesis of High Affinity Ligands for HIV Protease Inhibitors", *J. Org. Chem*, (1995), 6198-6201.

Ghosh, et al., "Cyclic Sulfone-3-Carboxamide as Novel P2-ligands for HIV-1 Protease Inhibitors", *Bioorganic and Med. Chem Letters*, (1995), 83-88.

Ghosh, et al., "Cyclic sulfones as novel and High Affinity P2-Ligands for HIV Protease Inhibitors", *J. Med, Chem*, 36, (1993), 924-927.

Ghosh, et al., "Darunavir (Prezista): A HIV-1 Protease Inhibitor for Treatment of Multidrug-Resistant HIV", *Modern Drug Synthesis*, Wiley, Edited by J. J. Li and D. S. Johnson, (2010), 29-44.

Ghosh, et al., "Darunavir, a Conceptually New HIV-1 Protease Inhibitor for the Treatment of Drug-resistant HIV", *Bioorg. Med. Chem*, 15, (2007), 7576.

Ghosh, et al., "Design and Synthesis of Stereochemically Defined Novel Spirocyclic P-2-Ligands for HIV-1 Protease Inhibitors", *Org. Lett*, 10(22), (2008), 5135-38.

Ghosh, et al., "Design of HIV Protease Inhibitors Targeting Protein Backbone: An Effective Strategy for Combating Drug Resistance", *Ace. Chem. Res*, 41(1), (2008), 78-86.

(56) References Cited

OTHER PUBLICATIONS

Ghosh, et al., "Design of HIV-1 Protease Inhibitors with Pyrrolidinones and Oxazolidinones as Novel P1'-Ligands to Enhance Backbone-binding interactions with Protease: Synthesis, Biological Evaluation and Protein-ligand X-ray Studies", *J. Med. Chem*, 52(13), (2009), 3902-3914.

Ghosh, et al., "Design, Synthesis, Protein-Ligand X-ray Structure, and Biological Evaluation of a Series of Novel Macrocyclic Human Immunodeficiency Virus-1 Protease Inhibitors to Combat Drug Resistance", *J. Med. Chem*, 52(23), (2009), 7689-7705.

Ghosh, et al., "Enantioselective Synthesis of Cyclopentyltetrahydrofuran (Cp-THF), an Important High-Affinity P2-Ligand for HIV-1 Protease Inhibitors", *Tetrajedron Lett*, 49(21), (2008), 3409-2412.

Ghosh, et al., "Flexible Cyclic Ethers/Polyethers as Novel P2-Ligands for HIV-1 Protease Inhibitors: Design, Synthesis, Biological Evaluation and Protein-ligand X-ray Studies", *J. Med. Chem*, 51(19), (2008), 6021-6033.

Ghosh, et al., "Harnessing Nature's Insight: Design of Aspartyl Protease Inhibitors from Treatment of Drug-Resistant HIV to Alzheimer's Disease", *J. Med. Chem*, (2009), 2163-2176.

Ghosh, et al., "HIV-1 Protease Inhibitors: Synthesis and biological Evalution of Glycopeptides", *Drug Design and Discovery*, (1993), 77-86.

Ghosh, et al., "Potent HIV Protease Inhibitors Incorporating the Development of Tetrahydrofuranylglycines as Novel P2-Ligands and Pyrazine Amides as P3-Ligands", *Journal of Medicinal Chemistry*, vol. 36, (1993), 2300-2310.

Ghosh, et al., "Potent HIV-1 Protease Inhibitors Incorporating meso-Bicyclic Urethanes as P2-ligands: Structure-Based Design, Synthesis, Biological Evaluation and Protein-Ligand X-Ray Studies", *Org. Biomol. Chem*, 6(20), (2008), 3703-3713.

Ghosh, et al., "Potent HIV-1 Protease Inhibitors: Stereoselective Synthesis of a New Dipeptide Mimic", *J. Org. Chem*, 58(5), (1993), 1025-1032.

Ghosh, et al., "Probing Multidrug-Resistance and Protein-Ligand Interactions with Oxatricyclic Designed Ligands in HIV-1 Protease Inhibitors", *ChemMedChem*, n/a. doi: 10.1002/cmdc.201000318, 1850-1854.

Ghosh, et al., "Ring-closing metathesis strategy to unsaturated γ- and δ-lactones: Synthesis of hydroxyethylene isostere for protease inhibitors", *Tetrahedron Letters*, 39(26), (1998), 4651-4654.

Ghosh, et al., "Severe Acute Respiratory Syndrome *Coronavirus* Papain-like Novel Protease Inhibitors: Design, Synthesis, Protein-Ligand X-ray Structure and Biological Evaluation", *J. Med. Chem*, 53(13), (2010), 4968-4979.

Ghosh, et al., "Stereocontrolled Synthesis of HIV-1 Protease Inhibitors with C2-Axis of Symmetry", *Tetrahedron Letters*, 32(41), (1991), 5729-33.

Ghosh, et al., "Stereoselective Photochemicail 1,3-Dioxolane Addition to 5-Aikoxyinethyl-2(5H)-furanone: Synthesis of Bis-tetrahydrofuranyl Ligand for HIV Protease Inhibitor UIC-94017 (TMC-114)", *J. Org. Chem*, (2004), 7822-29.

Ghosh, et al., "Structure Based Design of High Affinity Ligands for HIV-1 Protease Inhibitor: Replacements of Two Amides and a 10? Electron Aromatic System by a Fused Bis-tetrahydrofuran", *J. Med. Chem*, 37, (1994), 2506-08.

Ghosh, et al., "Structure Based Design: Synthesis and Biological Evaluation of a Series of Novel Cycloamide-Derived HIV-1 Protease Inhibitors", *J. Med. Chem.*, 48(10), 3576-3585.

Ghosh, et al., "Structure-based Design of Nonpeptide HIV Protease Inhibitors", *Farmaco*, 56, (2001), 29-32.

Ghosh, et al., "Structure-Based Design of Novel HIV-1 Protease Inhibitors to Combat Drug Resistance", *J. Med. Chem.*, vol. 49, (2006), 5252-5261.

Ghosh, et al., "Structure-Based Design, Synthesis, and Biological Evaluation of a Series of Novel and Reversible Inhibitors for the Severe Acute Respiratory Syndrome-*Coronavirus* Papain-Like Protease", *J. Med. Chem*, (2009), 5228-5240.

Ghosh, et al., "Syntheses of FDA Approved HIV Protease Inhibitors", *Synthesis* 2001(5), (2001), 2203-2229.

Ghosh, et al., "Synthesis and biological evaluation of novel allophenylnorstatine-based HIV-1 protease inhibitors incorporating high affinity P2-ligands", *Bioorg. Med, Chem Lett.*, 20(3), (2010), 1241-1246.

Ghosh, et al., "Synthesis and Optical Resolution of High Affinity P2-Ligands for HIV-1 Protease Inhibitors", *Tetrahedron Letters*, 36(4), (1995), 505-508.

Ghosh, et al., "The Development of Cyclic Sulfolanes as Novel and High Affinity P2-Ligands for HIV-1 Protease Inhibitors", *J. Med. Chern*, 37(8), (1994), 1177-1188.

Ghosh, et al., "TiCI4 Promoted Multi-component Reaction: A New Entry to the Functionalized a-Amino Acids", *Organic letters*, vol. 7, (2005), 7-10.

Ghosh, et al., "Transition-State Mimetics for HIV Protease Inhibitors: Stereocontrolled Synthesis of Hydroxyethylene and Hydroxyethylamine Isosteres by Ester Derived Titanium Enolate Syn- and Anti-aldol Reactions", *J. Org. Chern*, 63(18), (1998), 6146-6152.

Ghosh, A K, et al., "Design and synthesis of novel HIV-1 protease inhibitors incorporating oxyindoles as the P2-ligands", *Bioorganic & Medicinal Chemistry Letters*, vol. 16, (2006), 1869-1873.

Ghosh, A K, et al., "Nonpeptidal P2 Ligands for HIV Protease Inhibitors: Structure-Based Design, Synthesis, and Biological Evaluation", *J. Med. Chem.*, vol. 39, (1996), 3278-3290.

Ghosh, A K, et al., "Potent HIV protease inhibitors incorporating high-affinity P2-ligands and (R)-(hydroxyethylamino)sulfonamide isostere", *Bioorganic & Medicinal Chemistry Letters*, vol. 8, (1998), 687-690.

Ghosh, A K, et al., "Structure based design: novel spirocyclic ethers as nonpeptidal P2-ligands for HIV protease inhibitors", *Bioorganic & Medicinal Chemistry Letters*, vol. 8, (1998), 979-982.

Ghosh, K, et al., "Novel Cyclourethane-Derived HIV Protease Inhibitors: A Ring Closing Olefin Metathesis Based Strategy", *Bioorg. Med. Chem. Lett*, (2002), 1993-96.

Grabar, et al., "HIV infection in older patients in the HMRT era", Journal of Antimicrobial *Chemotherapy*, vol. 57, (2005), 4-7.

Hicks, Charles B, et al., "Durable Efficacy of Tipranavir-Ritonavir in Combination With an Optimised Background Regimen of Antiretroviral Drugs for Treatment-Experienced HIV-1-Infeced Patients AI 48 Weeks in the Randomized Evaluation of Strategic Intervention in Multi-Drug ReSistan", Patients With Tipranavir (RESIST) Studies: An Analysis of Combined Data From Two Randomised Open-Label Trials, *The Lancet*, vol. 368, (2006), 466-475.

Hirsch, et al., "Immune reconstitution in HIV-infected patients", *Clinical Infectious Diseases*, vol. 38, (2004), 1159-1166.

Holloway, et al., "Evaluating Scoring Functions for Docking and Designing Beta-Secretase Inhibitors", *Bioorganic and Medicinal A Chemistry Letters*, vol. 17, No. 3, (Jan. 19, 2007), 823-827.

Holloway, M K, et al., "A Priori Prediction of Activity for HIV-1 Protease Inhibitors Employing Energy Minimization in the Active Site", *J. Med. Chern*, 38(2), (1995), 305-317.

Hong, et al., "Crystal structure of an in vivo HIV-1 protease mutant in complex with saquinavir: insights into the mechanisms of drug resistance", *Protein Science*, vol. 9, (2000), 1898-1904.

Kaldor, Stephen W, et al., "Isophthalic acid derivatives: amino acid surrogates for the inhibition of HIV-1 protease", *Bioorganic & Medicinal Chemistry Letters* 5.7, (1995), 721-726.

Kaplan, et al., "Selection of multiple human immunodeficiency virus type 1 variants that encode viral proteases with decreased sensitivity to an inhibitor of the viral protease", *Proc. Natl. Acad. Sci. USA*, vol. 91, (1994), 5597-5601.

Koh, et al., "GRL-02031: A Novel Nonpeptide Protease Inhibitor (PI) Containing a Stereochemistry Defined Fused Cyclopentanyltetrahydrofuran (Cp-THF) Potent Against Multi-PI-Resistant HIV-1 In Vitro", *Antimicrobial Agents Chemother*, (2009), 987-996.

Koh, et al., "Novel bis tetrahydrofuranylurethane-containing nonpeptidic protease inhibitor (PI) UIC-94017 (TMC114) with

(56) References Cited

OTHER PUBLICATIONS potent activity against multi-PI-resistant human immunodeficiency virus in vitro", *Antimicrobial Aaents and Chemotheraov.* vol. 47 No. 10, (2003), 3123-3129.

Koh, Yasuhiro, et al., "Potent inhibition of HIV-1 replication by novel non-peptidyl small molecule inhibitors of protease dimerization", *J Biol Chem.*, 282(39), (Sep. 28, 2007), 28709-20.

Konvalinka, et al., "An Active-Site Mutation in the Human Immunodeficiency Virus Type 1 Proteinase (PR) Causes Reduced PR Activity and Loss of PR-Mediated Cytotoxicity without Apparent Effect on Virus Maturation and Infectivity", *Journal of Virology*, vol. 69, No. 11, (1995), 7180-7186.

Kortum, et al., "Potent and Selective Isophthalamide S2 Hydroxyethylamine Inhibitors fo BACE1", *Bioorganic and Medicinal Chemistry Letters*, vol. 17, No. 12, (Jun. 15, 2007), 3378-3383.

Kovalevsky, et al., "Effectiveness of nonpeptide clinical inhibitor TMG-114 on HIV-1 protease with highly drug resistant mutations D30N, I50V, and L90M", *J. Med. Chem.*, vol. 49, (2006), 1379-1387.

Kovalevsky, et al., "Solution Kinetics Measurements Suggest HIV-1 Protease Has Two Binding Sites for Darunavir and Amprenavir", *J. Med. Chem*, (2008), 6599-6503.

Kovalevsky, et al., "Structural Evidence for Effectiveness of Darunavir and Two Related Antiviral Inhibitors against HIV-2 Protease", *J.Mol. Biol*, (2008), 178-192.

Kovalevsky, et al., "Ultra-High Resolution Crystal Structure of HIV-1 Protease Mutant Reveals Two Binding Sites for ClinicalInhibitor TMC114", *J. Mol. Bioi.*, vol. 363, No. 1, (2006), 161-173.

Lapatto, et al., "X-Ray Analysis of HIV-1 Proteinase and 2.7 A Resolution Confirms Structural Homology Among Retroviral Enzymes", *Nature*, vol. 342, (1989), 299-302.

Levy, et al., "The Folding and Dimerization of HIV-1 Protease: Evidence for a Stable Monomer from Simulations", *J. Mol. Bioi.*, vol. 340, No. 1, (2004), 67-79.

Little, et al., "Antiretroviral-drug resistance among patients recently infected with HIV", *New England Journal of Medicine* vol. 347, No. 6, (2002), 385-394.

Liu, et al., "Effect of Flap Mutations on Structure of HIV-1 Protease and Inhibition by Saquinavir and Darunavir", *J. Mol. Biol*, 381(1), (2008), 102-115.

Louis, et al., "Revisiting Monomeric HIV-1 Protease", *J. Bioi. Chem.*, vol. 278, No. 8, (2003), 6085-6092.

Lshima, et al., "Folded Monomer of HIV-1 Protease", *J. Bioi. Chem.*, vol. 276, No. 52, (2001), 49110-49116.

Lshima, et al., "Solution Structure of the Mature HIV-1 Protease Monomer", *J. Bioi. Chem.*, vol. 278, No. 44, (2003), 43311-43319.

Maibaum, et al., "Inhibition of Porcine Pepsin by Two Substrate Analogues Containing Statine. The Effect of Histidine at the P2 Subsite on the Inhibition of Aspartic Proteinases", *J. Med. Chem.*, vol. 31, No. 34, (1988), 625-629.

Miller, et al., "Ultra-potent P1 modified arylsulfonamide HIV protease inhibitors: the discovery of GW0385", *Bioorganic & Medicinal Chemistr Letters*, vol. 16, (2006), 1788-1794.

Mitsuya, et al., "Development of Protease Inhibitors and the Fight with Drug-Resistant HIV-1 Variants", *Advances in Pharmacology*, (2007), 169-197.

Miyawaki, A, et al., "Fluorescent indicators for $Ca^{2+}$ based on green fluorescent proteins and calmodulin", *Nature*, 388(6645), (1997), 882-887.

Nakamura, et al., "Inhibitory Effects of Polyethers on Human Immunodeficiency Virus Replication", *Antimicrob. Agents Chemother*, (1992), 492-494.

Patick, et al., "Antiviral and Resistance Studies of AG1343, an Orally Bioavailable Inhibitor of Human Immunodeficiency Virus Protease", *Antimicrobial Agents and Chemotherapy*, vol. 40, No. 2, (1996), 292-297.

Poveda, et al., "Successful rescue therapy with darunabir (TMC114) in HlIV-infected patients who have failed several ritonavir-boosted protease inhibitors", *AIDS*, vol. 20, No. 11, (2006), 1558-1560.

Prabu-Jeyabalan, et al., "Mechanism of Substrate Recognition by Drug-Resistant Human Immunodeficiency Virus Type 1 Protease Variants Revealed by a Novel Structural Intermediate", *Journal of Virology*. vol. 80, No. 7, (2006), 3607-3616.

Sekar, et al., "Fluorescence Resonance Energy Transfer (FRET) Microscopy Imaging of Live Cell Protein Localizations", *J. Cell Biology*, vol. 160, No. 5, (2003), 629-633.

Sepkowitz, "AIDS—the first 20 years", *New England Journal of Medicine*, vol. 344, No. 23, (2001), 1764-1772.

Siegel, et al., "Fas Preassociation Required for Apoptosis Signaling and Dominant Inhibition by Pathogenic Mutations", *Science*, 2354, (2000).

Siliciano, et al., "A long-term latent reservoir for HIV-1: discovery and clinical implications", *Journal of Antimicrobial Chemotherapy*, vol. 54, (2004), 6-9.

Simon, et al., "HIV-1 dynamics in vivo: implications for therapy", *Nature Reviews Microbiology*, vol. 1, (2003), 181-190.

Stachel, et al., "Structure-based design of potent and selective cell-permeable inhibitors of human beta-secretase (BACE-1)", *Journal of Medicinal Chemistry*, vol. 47, No. 26, (Nov. 11, 2004), 6447-6450.

Staszewski, et al., "Efavirenz plus zidovudine and lamivudine, efavirenz plus indinavir, and indinavir plus zidovudine and tamivudine in the treatment of HIV-1 infection in adults", *New England Journal of Medicine*, vol. 341, No. 25, (1999), 1865-1873.

Szczesna-Skorupa, et al., "Fluorescence Resonance Energy Transfer Analysis of Cytochromes P450 2C2 and 2E1 Molecular Interactions in Living Cells", *Journal of Biological Chemistry*, vol. 278, No. 33, (2003), 31269-31276.

Thaisrivongs, et al., "Structure-Based Design of HIV Protease Inhibitors: Sulfonamide-Containing 5,6 Dihydro-4-hydroxy-2-pyrones as Non-Peptidic Inhibitors", *J. Med. Chern.*, vol. 39, No. 22, (1996), 4349-4353.

Thompson, W J, et al., "3'-Tetrahydrofuranglycine as a Novel, Unnatural Amino Acid Surrogate for Asparagine in the Design of Inhibitors of the HIV Protease", *J. Am. Chem. Soc*, (1993), 801-03.

Tie, et al., "Atomic Resolution crystal Structures of HIV-1 Protease and MutantsV82A and I84V with Saquinavir", *Proteins*, (2007), 232-242.

Tie, et al., "High Resolution Crystal Structures of HIV-1 Protease with a Potent-Non-Peptide Inhibitor (UIC-94017) Active Against Multi-Drug-Resistant Clinical Strains", *Journal of Molecular Biology*, vol. 338, (2004), 341-352.

Tojo, et al., "Novel Protease Inhibitors (PIs) Containing Macrocyclic Components and 3(R),3a(S),6a(R)-bis-Tetrahydrofuranylurethane (bis-THF) That Are Potent Against Multi-PI-Resistant HIV-1 Variants In Vitro", *Antimicrobial Agents and Chemotherapy*, (2010), 3460-3470.

Toth, et al., "A Simple, Continuous Fluorometric Assay for HIV Protease", *Int. J. Peptide Protein Res.*, 36, (1990), 544-550.

Wainberg, et al., "Public health implications of antiretroviral therapy and HIV drug resistance", *J. Am. Med. Assoc.*, vol. 279, (1998), 1977-1983.

Wang, et al., "Potent New Antiviral Compound Shows Similar inhibition and Structural Interactions with Drug Resistant Mutants and Wild Type HIV-1 Protease", *J. Med. Chem*, (2007), 4509.

Wlodawer, et al., "Conserved Folding in Retroviral Proteases: Crystal Structure of a Synthetic HIV-1 Protease", *Science*, vol. 245, (1989), 616-621.

Yoshimura, et al., "A Potent Human Immunodeficiency Virus Type 1 Protease Inhibitor, UIC-94003 (TMC-126), and Selection of a Novel (A28S) Mutation in the Protease Active Site", *Journal of Virology*, vol. 76, (2002), 1349-1358.

Yoshimura, et al., "JE-2147: a dipeptide protease inhibitor (PI) that potently inhibits multi-PI-resistant HIV-1", *Proc. Natl. Acad. Sci. USA*, vol. 96, (1999), 8675-8680.

Youle, et al., "Concomitant Use of an Active Boosted Protease Inhibitor with Enfuvirtide in Treatment-Experienced, HIV-Infected Individuals: Recent Data Consensus Recommendations", *HIV Clin. Trials*, vol. 7, No. 2, (2006), 86-96.

\* cited by examiner

NONPEPTIDE HIV-1 PROTEASE INHIBITORS

CROSS-REFERENCE TO RELATED APPLICATIONS

This application is a divisional of U.S. patent application Ser. No. 13/001,339, filed Mar. 31, 2011, which is a U.S. national application under 35 U.S.C. §371(b) of International Application Serial No. PCT/US2009/049407, filed Jul. 1, 2009 and published as WO 2010/002994 A1 on Jan. 7, 2010, which claims priority under 35 U.S.C. §119(e) to U.S. Provisional Application Ser. No. 61/077,343, filed on Jul. 1, 2008, the disclosures of all of which are incorporated by reference in their entirety.

GOVERNMENT RIGHTS

This invention was made with government support under grant number GM053386 awarded by the National Institutes of Health. The government has certain rights in the invention.

TECHNICAL FIELD

This invention pertains to the field of non-peptide inhibitors of HIV protease enzymes and their use in the treatment of HIV infections.

BACKGROUND AND SUMMARY OF THE INVENTION

The AIDS epidemic is one of the most challenging problems in medicine in the 21st century. A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a vitally encoded protease to generate mature vital proteins required for virus assembly and function. Inhibition of this processing prevents the production of normally infectious virus. It has been previously demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

Among many strategies to combat this disease, highly active antiretroviral therapy (HAART) with HIV protease inhibitors (PIs) in combination with reverse transcriptase inhibitors (RTIs) continues to be the first line treatment for control of HIV infection. This treatment regimen has definitely improved quality of life, enhanced HIV management, and halted the progression of the disease. However, despite these impressive successes, there remain many challenges to treating this devastating disease, including decreasing both the toxicity of and complexity of these treatment regimens. In addition, there is a growing population of patients that are developing multi-drug resistant strains of HIV, and there is ample evidence that these strains can be further transmitted.

HAART has had a major impact on the AIDS epidemic in industrially advanced nations; however, eradication of human immunodeficiency virus type 1 (HIV 1) appears to be currently unachieved, in part due to the viral reservoirs remaining in blood and infected tissues. The limitation of antiviral therapy of AIDS is also exacerbated by complicated regimens, the development of drug-resistant HIV-1 variants, and a number of inherent adverse effects. However, a number of challenges have nonetheless been encountered in bringing about the optimal benefits of the currently available therapeutics of AIDS and HIV-1 infection to individuals receiving HAART. They include (i) drug-related toxicities; (ii) partial restoration of immunologic functions once individuals developed AIDS; (iii) development of various cancers as a consequence of survival prolongation; (iv) flame-up of inflammation in individuals receiving HAART or immune re-construction syndrome (IRS); and (v) increased cost of antiviral therapy. Such limitations of HAART are exacerbated by the development of drug-resistant HIV-1 variants.

Without being bound by theory, it is believed that successful antiviral drugs exert their virus-specific effects by interacting with viral receptors, virally encoded enzymes, viral structural components, viral genes, or their transcripts without disturbing cellular metabolism or function. However, at present, it is believed that current antiretroviral drugs and agents are unlikely to be completely specific for HIV-1 or to be devoid of toxicity or side effects in the therapy of AIDS. Those issues are of special note because patients with AIDS and its related diseases will have to receive antiretroviral therapy for a long period of time, perhaps for the rest of their lives.

The invention described herein includes novel compounds and compositions for treating patients in need of relief from HIV, AIDS, and AIDS-related diseases. In addition, the invention described herein includes methods for treating HIV, AIDS, and AIDS-related diseases using the compounds described herein as well as known compounds that heretofore have not been used or described as being useful in the treatment of such diseases.

The compounds described herein may be used in the treatment of HIV, AIDS, and AIDS-related diseases. Without being bound by theory, it is suggested that the compounds described herein may exert their utility by the inhibition of proteases encoded by human immunodeficiency virus (HIV), such as HIV-1. The compounds or pharmaceutically acceptable salts thereof, are of value in the prevention of infection by HIV, the treatment of infection by HIV and the treatment of the resulting acquired immune deficiency syndrome (AIDS), either as compounds, pharmaceutically acceptable salts, or pharmaceutical composition ingredients. It is appreciated that the compounds described herein may be used alone or in combination with other compounds useful for treating such diseases, including those compounds that may operate by the same or different modes of action. Further, it is appreciated that the compounds and compositions described herein may be administered alone or with other compounds and compositions, such as other antivirals, immunomodulators, antibiotics, vaccines, and the like.

In one illustrative embodiment, a compound of the following Formula I is described.

Formula I

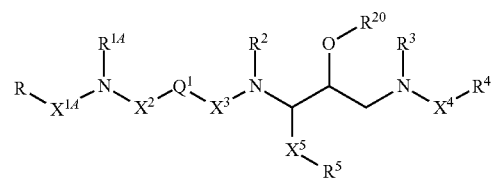

or a pharmaceutically acceptable salt, isomer, mixture of isomers, crystalline form, non crystalline form, hydrate, or solvate thereof; wherein R is hydrogen, alkyl, cycloalkyl, heterocycloalkyl, aryl, arylalkyl, heteroaryl, or heteroarylalkyl, each of which is optionally substituted;

$Q^1$ is a cycloalkylene, heterocycloalkylene, arylene, or heteroarylene, each of which is optionally substituted;

$X^{1A}$ is a bond, —N($R^{17}$)—, —S(O)$_q$—, or optionally substituted alkylene; and $R^{1A}$ is —S(O)$_2R^{14}$, —C(O)$R^{12}$, —N($R^8$)$R^9$, alkyl, cycloalkyl, cycloalkyl-alkyl, heterocycloalkyl, heterocycloalkyl-alkyl, aryl, arylalkyl, heteroaryl, or heteroarylalkyl, each of which is optionally substituted, or $R^{1A}$ and $X^{1A}$ together with the attached nitrogen form an optionally substituted heterocyclyl;

$X^2$ is —C(O)—, —S(O)$_n$—, or optionally substituted alkylene;

$X^3$ is —C(O)— or —S(O)$_p$—;

$X^4$ is a bond, —C(O)—, —S(O)$_q$—, —N($R^{17}$)—, optionally substituted alkylene, —CH(C(O)$R^{12}$)—, or —CH(S(O)$_n$ $R^{11}$)—;

$X^5$ is a bond, —N($R^{17}$)—, —S(O)$_q$—, or optionally substituted alkylene;

$R^2$ and $R^3$ are each independently selected from the group consisting of hydrogen, —S(O)$_2R^{14}$, —C(O)$R^{12}$, —N($R^8$)$R^9$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; $R^4$ and $R^5$ are each independently selected from the group consisting of hydrogen, halogen, —OH, —NO$_2$, —N($R^8$)$R^9$, —OR$^{10}$, —S(O)$_nR^{11}$, —C(O)$R^{12}$, alkyl, cycloalkyl, heterocycloalkyl, aryl, and heteroaryl, each of which is optionally substituted; or $R^3$, $R^4$, $X^4$ and the attached nitrogen form an optionally substituted heterocyclyl;

p is independently 1 or 2 in each instance; and n and q are each independently 0, 1, or 2 in each instance;

$R^{20}$ is hydrogen, or a prodrug forming group;

$R^8$ is in each instance independently selected from the group consisting of hydrogen, —C(O)$R^{13}$, —S(O)$_2R^{14}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^9$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{10}$ is in each instance independently selected from the group consisting of —C(O)$R^{13}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{11}$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 0; $R^{11}$ is in each instance independently selected from the group consisting of alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 1; and $R^{11}$ is in each instance independently selected from the group consisting of —N($R^{15}$)$R^{16}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 2;

$R^{12}$ and $R^{13}$ are each independently selected from the group consisting of hydrogen, —OR$^{19}$, —N($R^{18}$)$R^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{14}$ is in each instance independently selected from the group consisting of hydrogen, —N($R^{18}$)$R^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; and $R^{15}$, $R^{16}$, $R^{17}$, $R^{18}$, and $R^{19}$ are in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

with the proviso that the compound is not

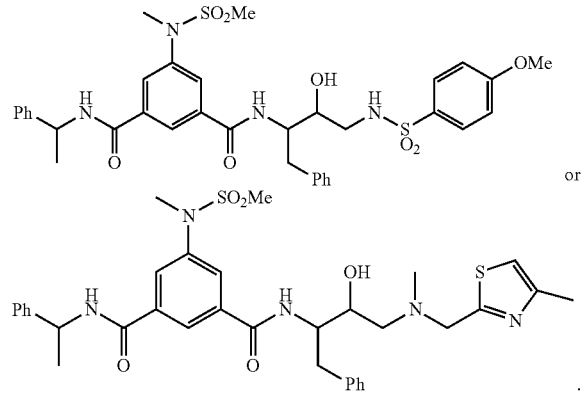

In another illustrative embodiment, a compound of the following Formula II is described.

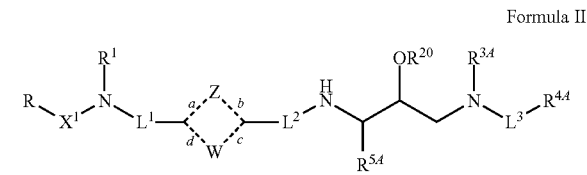

Formula II and solvates, hydrates and pharmaceutically acceptable salts thereof; wherein:

W and Z are independently selected from the group consisting of a bond and a divalent group $CR^A$, $CR^A_2$, N, $NR^A$, O, $S(O)_m$ and covalently bonded combinations thereof; where m is an integer from 0 to 2; providing that neither W nor Z comprises O—O, or O—S(O); and providing that W, Z, and the attached carbons form at least a five-membered ring;

bonds a, b, c, and d are each independently selected from the group consisting single bond, double bond, and aromatic bond;

$R^A$ is in each instance independently selected from the group consisting of hydrogen, alkyl, alkenyl, heteroalkyl, cycloalkyl, heterocyclyl, halo, nitro, cyano, $OR^{13A}$, $SR^{13A}$, $S(O)R^{13A}$, $SO_2R^{13A}$, $NR^{13A}R^{14A}$, $CO_2R^{13A}$, $CONR^{13A}R^{14A}$, aryl, heteroaryl, arylalkyl, and heteroarylalkyl, each of which is optionally substituted; where $R^{13A}$ and $R^{14A}$ are each independently selected in each instance from the group consisting of hydrogen, alkyl, alkenyl, heteroalkyl, cycloalkyl, heterocyclyl, aryl, arylalkyl, heteroaryl, and heteroarylalkyl, each of which is optionally substituted, or $R^{13A}$ and $R^{14A}$ together with the attached nitrogen form an optionally substituted heterocyclyl;

$R^1$ is hydrogen, alkyl, alkenyl, heteroalkyl, cycloalkyl, heterocyclyl, aryl, arylalkyl, heteroaryl, or heteroarylalkyl, each of which is optionally substituted; and $X^1$ is a bond, alkylene, heteroalkylene, cycloalkylene, or cycloheteroalkylene, each of which is optionally substituted; or $R^1$ and $X^1$ together with the attached nitrogen form an optionally substituted heterocyclyl;

R is hydrogen, alkyl, alkenyl, heteroalkyl, cycloalkyl, heterocyclyl, aryl, arylalkyl, heteroaryl or heteroarylalkyl, each of which is optionally substituted;

$L^1$ is —C(O)—, —OC(O)—, —NR$^7$C(O)—, —S(O)$_n$—, or —CR$^7$R$^{8A}$—; where n is 1 or 2; and $R^7$ and $R^{8A}$ are each independently selected from the group consisting of hydrogen, alkyl, alkenyl, hetero alkyl, cycloalkyl, heterocyclyl, aryl, arylalkyl, heteroaryl and heteroarylalkyl, each of which is optionally substituted, or $R^7$ and $R^{8A}$ together with the carbon atom to which they are attached form an optionally substituted cycloalkyl;

$L^2$ is —C(O)— or —S(O)$_p$—, where p is 1 or 2;

$R^{5A}$ is alkyl, alkenyl, heteroalkyl, cycloalkyl, heterocyclyl, aryl, arylalkyl, heteroaryl or heteroarylalkyl, each of which is optionally substituted;

$R^{20}$ is independently in each instance hydrogen or a pro-drug moiety;

$L^3$ is —C(O)—, —C(O)O—, —C(O)NR$^4$—, —NR$^{20}$C(O)—, —S(O)$_q$—, —NR$^{20}$S(O)$_q$—, optionally substituted alkylene, —CH(C(O)NR$^{9A}$R$^{10A}$)—, —CH(C(O)OR$^{9A}$)—, or —CH(S(O)$_r$R$^{9A}$)—; where q is 1 or 2; r is an integer from 0 to 2; and $R^{9A}$ and $R^{10A}$ are each independently selected from the group consisting of hydrogen, alkyl, alkenyl, heteroalkyl, cycloalkyl, heterocyclyl, aryl, arylalkyl, heteroaryl and heteroarylalkyl, each of which is optionally substituted, or $R^{9A}$ and $R^{10A}$ together with the attached nitrogen form an optionally substituted heterocyclyl; and $R^{4A}$ is cycloalkyl, heterocyclyl, aryl, or heteroaryl, each of which is optionally substituted; and $R^{3A}$ is hydrogen, alkyl, alkenyl, heteroalkyl, arylalkyl, heteroarylalkyl, heterocyclylalkyl, each of which is optionally substituted, —NR$^{20}$R$^{6a}$, -alkylene-SR$^{11A}$-alkylene-OR$^{11A}$, -alkylene-NR$^{11A}$R$^{12A}$; where $R^{6a}$ is hydrogen, alkyl, alkenyl, heteroalkyl, arylalkyl, heteroarylalkyl, heterocyclylalkyl, each of which is optionally substituted, -alkylene-SR$^{11A}$, -alkylene-OR$^{11A}$, or -alkylene-NR$^{11A}$R$^{12A}$; where $R^{11A}$ and $R^{12A}$ are each independently selected from the group consisting of hydrogen, alkyl, alkenyl, heteroalkyl, cycloalkyl, heterocyclyl, aryl, arylalkyl, heteroaryl and heteroarylalkyl, each of which is optionally substituted; or $R^{11A}$ and $R^{12A}$ together with the attached nitrogen form an optionally substituted heterocyclyl; or $R^{4A}$ and $R^{3A}$ together with $L^3$ and the attached nitrogen form an optionally substituted mono or bicyclic heterocycle;

providing that the compound is not

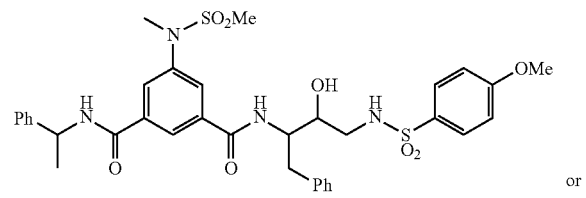

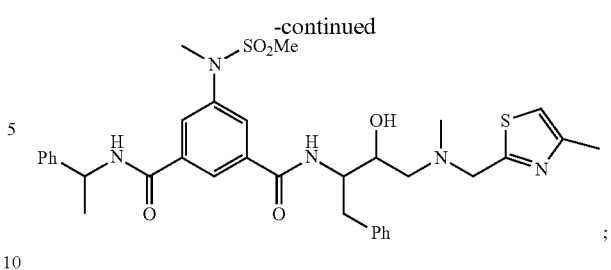

and providing that when $L^3$ is C(O), $R^{4A}$ is aryl, or heteroaryl, each of which is optionally substituted, or $R^{4A}$ and $R^{3A}$ together with $L^3$ and the attached nitrogen form an optionally substituted heterocycle.

In another illustrative embodiment, a compound of the following Formula III is described.

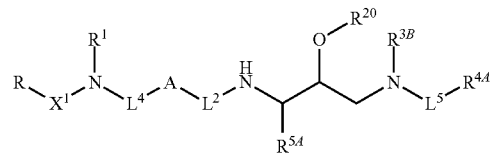

Formula III and solvates, hydrates and pharmaceutically acceptable salts thereof; wherein:

A is a divalent aromatic group;

$R^1$ is hydrogen, alkyl, alkenyl, heteroalkyl, cycloalkyl, heterocyclyl, aryl, arylalkyl, heteroaryl, or heteroarylalkyl, each of which is optionally substituted; and $X^1$ is a bond, alkylene, heteroalkylene, cycloalkylene, or cycloheteroalkylene, each of which is optionally substituted; or $R^1$ and $X^1$ together with the attached nitrogen form an optionally substituted heterocyclyl;

R is hydrogen, alkyl, alkenyl, heteroalkyl, cycloalkyl, heterocyclyl, aryl, arylalkyl, heteroaryl or heteroarylalkyl, each of which is optionally substituted;

$L^4$ is —C(O)—, —S(O)$_n$—, or —CR$^7$R$^{8A}$—; where n is 1 or 2; $R^7$ and $R^{8A}$ are each independently selected from the group consisting of hydrogen, alkyl, alkenyl, heteroalkyl, cycloalkyl, heterocyclyl, aryl, arylalkyl, heteroaryl and heteroarylalkyl, or $R^7$ and $R^{8A}$ together with the carbon atom to which they are attached form an cycloalkyl, each of which is optionally substituted;

$L^2$ is —C(O)— or —S(O)$_p$—, where p is 1 or 2;

$R^{5A}$ is alkyl, alkenyl, heteroalkyl, cycloalkyl, heterocyclyl, aryl, arylalkyl, heteroaryl or heteroarylalkyl, each of which is optionally substituted;

$R^{20}$ is hydrogen or a pro-drug moiety;

$L^5$ is —C(O)—, —S(O)$_q$—, NR$^{9A}$, optionally substituted alkylene, —CH(C(O)NR$^{9A}$R$^{10A}$)—, —CH(C(O)OR$^{9A}$)—, or —CH(S(O)$_r$R$^{9A}$)—; where q is 1 or 2; r is an integer from 0 to 2; and $R^{9A}$ and $R^{10A}$ are each independently selected from the group consisting of hydrogen, alkyl, alkenyl, heteroalkyl, cycloalkyl, heterocyclyl, aryl, arylalkyl, heteroaryl and heteroarylalkyl, each of which is optionally substituted, or $R^{9A}$ and $R^{10A}$ together with the attached nitrogen form an optionally substituted heterocyclyl;

$R^{4A}$ is cycloalkyl, heterocyclyl, aryl, or heteroaryl, each of which is optionally substituted; $R^{3B}$ is hydrogen, alkyl, alkenyl, heteroalkyl, arylalkyl, heteroarylalkyl, heterocyclylalkyl, each of which is optionally substituted, -alkylene- $SR^{11A}$, alkylene-$OR^{11A}$ or -alkylene-$NR^{11A}R^{12A}$, where $R^{11A}$ and $R^{12A}$ are each independently selected from the group consisting of hydrogen, alkyl, alkenyl, heteroalkyl, cycloalkyl, heterocyclyl, aryl, arylalkyl, heteroaryl and heteroarylalkyl, each of which is optionally substituted, or $R^{11A}$ and $R^{12A}$ together with the attached nitrogen form an optionally substituted heterocyclyl; or $R^{4A}$ and $R^{3B}$ together with $L^5$ and the attached nitrogen form an optionally substituted heterocycle;

with the proviso that the compound is not

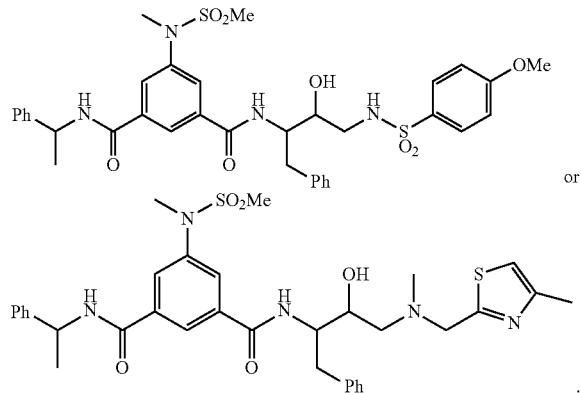

In another embodiment, methods for treating AIDS, HIV, and other AIDS-related diseases are described herein, where the method includes the step of administering to a patient in need of relief from the disease a therapeutically effective amount or one or more compounds of Formulae I, II, and/or III.

In another embodiment, methods for treating AIDS, HIV, and other AIDS-related diseases are described herein, where the method includes the step of administering to a patient in need of relief from the disease a therapeutically effective amount of one or more compounds of Formula IV, or a composition containing one or more compounds of Formula IV Formula IV

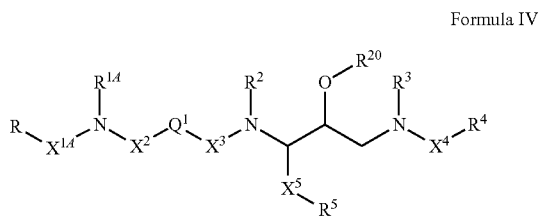

or a pharmaceutically acceptable salt, isomer, mixture of isomers, crystalline form, non crystalline form, hydrate, or solvate thereof; wherein R is hydrogen, alkyl, cycloalkyl, heterocycloalkyl, aryl, arylalkyl, heteroaryl, or heteroarylalkyl, each of which is optionally substituted;

$Q^1$ is a cycloalkylene, heterocycloalkylene, arylene, or heteroarylene, each of which is optionally substituted;

$X^{1A}$ is a bond, —$N(R^{17})$—, —$S(O)_q$—, or optionally substituted alkylene; and $R^{1A}$ is —$S(O)_2R^{14}$, —$C(O)R^{12}$, —$N(R^8)R^9$, alkyl, cycloalkyl, cycloalkyl-alkyl, heterocycloalkyl, heterocycloalkyl-alkyl, aryl, arylalkyl, heteroaryl, or heteroarylalkyl, each of which is optionally substituted, or $R^{1A}$ and $X^{1A}$ together with the attached nitrogen form an optionally substituted heterocyclyl;

$X^2$ is —$C(O)$—, —$S(O)_n$—, or optionally substituted alkylene;

$X^3$ is —$C(O)$— or —$S(O)_p$—;

$X^4$ is a bond, —$C(O)$—, —$S(O)_q$—, —$N(R^{17})$—, optionally substituted alkylene, —$CH(C(O)R^{12})$—, or —$CH(S(O)_n R^{11})$—;

$X^5$ is a bond, —$N(R^{17})$—, —$S(O)_q$—, or optionally substituted alkylene;

$R^2$ and $R^3$ are each independently selected from the group consisting of hydrogen, —$S(O)_2R^{14}$, —$C(O)R^{12}$, —$N(R^8)R^9$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; $R^4$ and $R^5$ are each independently selected from the group consisting of hydrogen, halogen, —OH, —$NO_2$, —$N(R^8)R^9$, —$S(O)_n R^{11}$, —$C(O)R^{12}$, alkyl, cycloalkyl, heterocycloalkyl, aryl, and heteroaryl, each of which is optionally substituted; or $R^3$, $R^4$, $X^4$ and the attached nitrogen form an optionally substituted heterocyclyl;

p is independently 1 or 2 in each instance; and n and q are each independently 0, 1, or 2 in each instance;

$R^{20}$ is hydrogen, or a prodrug forming group;

$R^8$ is in each instance independently selected from the group consisting of hydrogen, —$C(O)R^{13}$, —$S(O)_2R^{14}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^9$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{10}$ is in each instance independently selected from the group consisting of —$C(O)R^{13}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{11}$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 0; $R^{11}$ is in each instance independently selected from the group consisting of alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 1; and $R^{11}$ is in each instance independently selected from the group consisting of —$N(R^{15})R^{16}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 2;

$R^{12}$ and $R^{13}$ are each independently selected from the group consisting of hydrogen, —$OR^{19}$, —$N(R^{18})R^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{14}$ is in each instance independently selected from the group consisting of hydrogen, —$N(R^{18})R^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; and $R^{15}$, $R^{16}$, $R^{17}$, $R^{18}$, and $R^{19}$ are in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted.

In another embodiment, pharmaceutical compositions comprising one or more compounds of Formulae I, II and/or III are described herein.

DETAILED DESCRIPTION

In one illustrative embodiment, a compound of the following Formula I is described.

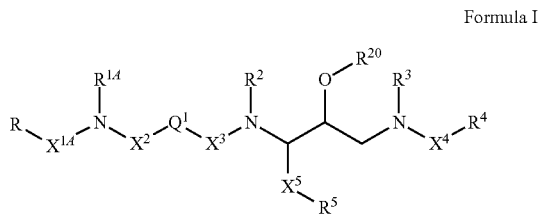

Formula I or a pharmaceutically acceptable salt, isomer, mixture of isomers, crystalline form, non crystalline form, hydrate, or solvate thereof; wherein R is hydrogen, alkyl, cycloalkyl, heterocycloalkyl, aryl, arylalkyl, heteroaryl, or heteroarylalkyl, each of which is optionally substituted;

$Q^1$ is a cycloalkylene, heterocycloalkylene, arylene, or heteroarylene, each of which is optionally substituted;

$X^{1A}$ is a bond, —N($R^{17}$)—, —S(O)$_q$—, or optionally substituted alkylene; and $R^{1A}$ is —S(O)$_2R^{14}$, —C(O)$R^{12}$, —N($R^8$)$R^9$, alkyl, cycloalkyl, cycloalkyl-alkyl, heterocycloalkyl, heterocycloalkyl-alkyl, aryl, arylalkyl, heteroaryl, or heteroarylalkyl, each of which is optionally substituted, or $R^{1A}$ and $X^{1A}$ together with the attached nitrogen form an optionally substituted heterocyclyl;

$X^2$ is —C(O)—, —S(O)$_n$—, or optionally substituted alkylene;

$X^3$ is —C(O)— or —S(O)$_p$—;

$X^4$ is a bond, —C(O)—, —S(O)$_q$—, —N($R^{17}$)—, optionally substituted alkylene, —CH(C(O)$R^{12}$)—, or —CH(S(O)$_n R^{11}$)—;

$X^5$ is a bond, —N($R^{17}$)—, —S(O)$_q$—, or optionally substituted alkylene;

$R^2$ and $R^3$ are each independently selected from the group consisting of hydrogen, —S(O)$_2R^{14}$, —C(O)$R^{12}$, —N($R^8$)$R^9$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; $R^4$ and $R^5$ are each independently selected from the group consisting of hydrogen, halogen, —OH, —NO$_2$, —N($R^8$)$R^9$, —OR$^{10}$, —S(O)$_n R^{11}$, —C(O)$R^{12}$, alkyl, cycloalkyl, heterocycloalkyl, aryl, and heteroaryl, each of which is optionally substituted; or $R^3$, $R^4$, $X^4$ and the attached nitrogen form an optionally substituted heterocyclyl;

p is independently 1 or 2 in each instance; and n and q are each independently 0, 1, or 2 in each instance;

$R^{20}$ is hydrogen, or a prodrug forming group;

$R^8$ is in each instance independently selected from the group consisting of hydrogen, —C(O)$R^{13}$, —S(O)$_2R^{14}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^9$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{10}$ is in each instance independently selected from the group consisting of —C(O)$R^{13}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{11}$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 0; $R^{11}$ is in each instance independently selected from the group consisting of alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 1; and $R^{11}$ is in each instance independently selected from the group consisting of —N($R^{15}$)$R^{16}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 2;

$R^{12}$ and $R^{13}$ are each independently selected from the group consisting of hydrogen, —OR$^{19}$, —N($R^{18}$)$R^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{14}$ is in each instance independently selected from the group consisting of hydrogen, —N($R^{18}$)$R^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; and $R^{15}$, $R^{16}$, $R^{17}$, $R^{18}$, and $R^{19}$ are in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

with the proviso that the compound is not

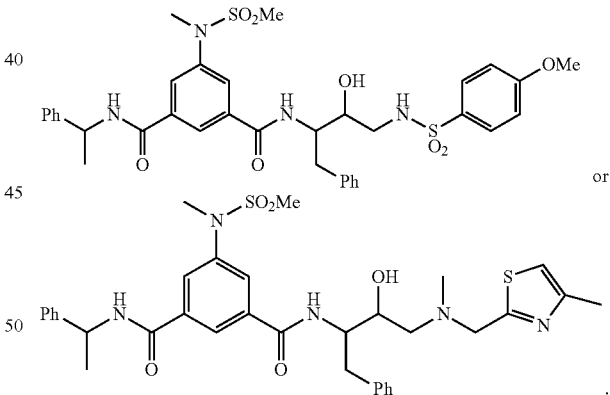

In another embodiment, a compound of Formula I, or a pharmaceutically acceptable salt, isomer, mixture of isomers, crystalline form, non crystalline form, hydrate, or solvate thereof is described herein;

wherein

R is hydrogen, alkyl, cycloalkyl, heterocycloalkyl, aryl, arylalkyl, heteroaryl, or heteroarylalkyl, each of which is optionally substituted;

$Q^1$ is a cycloalkylene, heterocycloalkylene, arylene, or heteroarylene, each of which is optionally substituted;

$X^{1A}$ is a bond, —C(O)—, —N($R^{17}$)—, —S(O)$_q$—, or optionally substituted alkylene; and $R^{1A}$ is —S(O)$_2R^{14}$, —C(O)$R^{12}$, —N($R^8$)$R^9$, alkyl, cycloalkyl, cycloalkyl-alkyl, heterocycloalkyl, heterocycloalkyl-alkyl, aryl, arylalkyl, heteroaryl, or heteroarylalkyl, each of which is optionally substituted, or $R^{14}$ and $X^{14}$ together with the attached nitrogen form an optionally substituted heterocyclyl;

$X^2$ is a bond, —C(O)—, —S(O)$_n$—, or optionally substituted alkylene;

$X^3$ is —C(O)— or —S(O)$_p$—;

$X^4$ is a bond, —C(O)—, —S(O)$_q$—, —N(R$^{17}$)—, optionally substituted alkylene, —CH(C(O)R$^{12}$)—, or —CH(S(O)$_n$R$^{11}$)—;

$X^5$ is a bond, —N(R$^{17}$)—, —S(O)$_q$—, or optionally substituted alkylene;

$R^2$ and $R^3$ are each independently selected from the group consisting of hydrogen, —S(O)$_2$R$^{14}$, —C(O)R$^{12}$, —N(R$^8$)R$^9$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; $R^4$ and $R^5$ are each independently selected from the group consisting of hydrogen, halogen, —OH, —NO$_2$, —N(R$^8$)R$^9$, —OR$^{10}$, —S(O)$_n$R$^{11}$, —C(O)R$^{12}$, alkyl, cycloalkyl, heterocycloalkyl, aryl, and heteroaryl, each of which is optionally substituted; or $R^3$, $R^4$, $X^4$ and the attached nitrogen form an optionally substituted heterocyclyl;

p is independently 1 or 2 in each instance; and n and q are each independently 0, 1, or 2 in each instance;

$R^{20}$ is hydrogen, or a prodrug forming group;

$R^8$ is in each instance independently selected from the group consisting of hydrogen, —C(O)R$^{13}$, —S(O)$_2$R$^{14}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^9$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{10}$ is in each instance independently selected from the group consisting of —C(O)R$^{13}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{11}$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 0; $R^{11}$ is in each instance independently selected from the group consisting of alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 1; and $R^{11}$ is in each instance independently selected from the group consisting of —N(R$^{15}$)R$^{16}$, alkyl, cycloalkyl, cycloalkyl-alkyl, heterocycloalkyl, heterocycloalkyl-alkyl, aryl, aryl alkyl, heteroaryl, and heteroarylalkyl, each of which is optionally substituted, when n is 2;

$R^{12}$ and $R^{13}$ are each independently selected from the group consisting of hydrogen, —OR$^{19}$, —N(R$^{18}$)R$^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{14}$ is in each instance independently selected from the group consisting of hydrogen, —N(R$^{18}$)R$^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; and $R^{15}$, $R^{16}$, $R^{17}$, $R^{18}$, and $R^{19}$ are in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

with the proviso that the compound is not

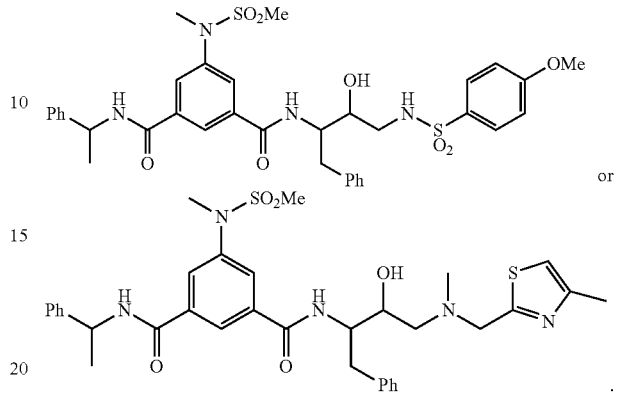

In another illustrative embodiment, a compound of the preceding embodiment is described herein wherein $X^{1A}$—N(R$^{1A}$)—$X^2$-$Q^1$-$X^3$ are taken to form C(O)—N(R$^{1A}$)-$Q^1$-C(O); and $Q^1$ is an optionally substituted 1,4-arylene.

In another illustrative embodiment, compounds, pharmaceutical compositions containing such compounds, and methods for using compounds of the preceding embodiment are described herein wherein $X^{1A}$—N(R$^{1A}$)—$X^2$-$Q^1$-$X^3$ are taken to form C(O)—N(R$^{1A}$)-$Q^1$-C(O); and $Q^1$ is an optionally substituted 1,4-phenylene;

In another illustrative embodiment, a compound of the following Formula II is described.

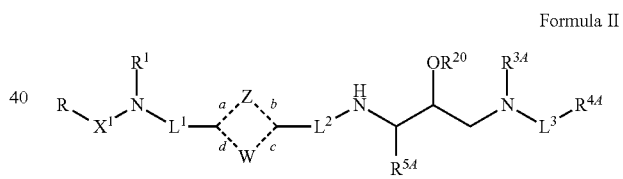

Formula II and solvates, hydrates and pharmaceutically acceptable salts thereof; wherein:

W and Z are independently selected from the group consisting of a bond and a divalent group CR$^A$, CR$^A_2$, N, NR$^A$, O, S(O)$_m$ and covalently bonded combinations thereof; where m is an integer from 0 to 2; providing that neither W nor Z comprises O—O, or O—S(O); and providing that W, Z, and the attached carbons form at least a five-membered ring;

bonds a, b, c, and d are each independently selected from the group consisting single bond, double bond, and aromatic bond;

$R^A$ is in each instance independently selected from the group consisting of hydrogen, alkyl, alkenyl, heteroalkyl, cycloalkyl, heterocyclyl, halo, nitro, cyano, OR$^{13A}$, SR$^{13A}$, S(O)R$^{13A}$, SO$_2$R$^{13A}$, NR$^{13A}$R$^{14A}$, CO$_2$R$^{13A}$, CONR$^{13A}$R$^{14A}$, aryl, heteroaryl, arylalkyl, and heteroarylalkyl, each of which is optionally substituted; where $R^{13A}$ and $R^{14A}$ are each independently selected in each instance from the group consisting of hydrogen, alkyl, alkenyl, heteroalkyl, cycloalkyl, heterocyclyl, aryl, arylalkyl, heteroaryl, and heteroarylalkyl, each of which is optionally substituted, or $R^{13A}$ and $R^{14A}$ together with the attached nitrogen form an optionally substituted heterocyclyl;

$R^1$ is hydrogen, alkyl, alkenyl, heteroalkyl, cycloalkyl, heterocyclyl, aryl, arylalkyl, heteroaryl, or heteroarylalkyl, each of which is optionally substituted; and $X^1$ is a bond, alkylene, heteroalkylene, cycloalkylene, or cycloheteroalkylene, each of which is optionally substituted; or $R^1$ and $X^1$ together with the attached nitrogen form an optionally substituted heterocyclyl;

R is hydrogen, alkyl, alkenyl, heteroalkyl, cycloalkyl, heterocyclyl, aryl, arylalkyl, heteroaryl or heteroarylalkyl, each of which is optionally substituted;

$L^1$ is —C(O)—, —OC(O)—, —NR$^7$C(O)—, —S(O)$_n$—, or —CR$^7$R$^{8A}$—; where n is 1 or 2; and $R^7$ and $R^{8A}$ are each independently selected from the group consisting of hydrogen, alkyl, alkenyl, heteroalkyl, cycloalkyl, heterocyclyl, aryl, arylalkyl, heteroaryl and heteroarylalkyl, each of which is optionally substituted, or $R^7$ and $R^{8A}$ together with the carbon atom to which they are attached form an optionally substituted cycloalkyl;

$L^2$ is —C(O)— or —S(O)$_p$—, where p is 1 or 2;

$R^{5A}$ is alkyl, alkenyl, heteroalkyl, cycloalkyl, heterocyclyl, aryl, arylalkyl, heteroaryl or heteroarylalkyl, each of which is optionally substituted;

$R^{20}$ is independently in each instance hydrogen or a pro-drug moiety;

$L^3$ is —C(O)—, —C(O)O—, —C(O)NR$^4$—, —NR$^{20}$C(O)—, —S(O)$_q$—, —NR$^{20}$S(O)$_q$—, optionally substituted alkylene, —CH(C(O)NR$^{9A}$R$^{10A}$)—, —CH(C(O)OR$^{9A}$)—, or —CH(S(O)$_r$R$^{9A}$)—; where q is 1 or 2; r is an integer from 0 to 2; and $R^{9A}$ and $R^{10A}$ are each independently selected from the group consisting of hydrogen, alkyl, alkenyl, heteroalkyl, cycloalkyl, heterocyclyl, aryl, arylalkyl, heteroaryl and heteroarylalkyl, each of which is optionally substituted, or $R^{9A}$ and $R^{10A}$ together with the attached nitrogen form an optionally substituted heterocyclyl; and $R^{4A}$ is cycloalkyl, heterocyclyl, aryl, or heteroaryl, each of which is optionally substituted; and $R^{3A}$ is hydrogen, alkyl, alkenyl, heteroalkyl, arylalkyl, heteroarylalkyl, heterocyclyalkyl, each of which is optionally substituted, —NR$^{20}$R$^{6a}$, -alkylene-SR$^{11A}$, -alkylene-OR$^{11A}$, -alkylene-NR$^{11A}$R$^{12A}$; where $R^{6a}$ is hydrogen, alkyl, alkenyl, heteroalkyl, arylalkyl, heteroarylalkyl, heterocyclylalkyl, each of which is optionally substituted, -alkylene-SR$^{11A}$, -alkylene-OR$^{11A}$, or -alkylene-NR$^{11A}$R$^{12A}$; where $R^{11A}$ and $R^{12A}$ are each independently selected from the group consisting of hydrogen, alkyl, alkenyl, heteroalkyl, cycloalkyl, heterocyclyl, aryl, arylalkyl, heteroaryl and heteroarylalkyl, each of which is optionally substituted; or $R^{11A}$ and $R^{12A}$ together with the attached nitrogen form an optionally substituted heterocyclyl; or $R^{4A}$ and $R^{3A}$ together with $L^3$ and the attached nitrogen form an optionally substituted mono or bicyclic heterocycle;

providing that the compound is not

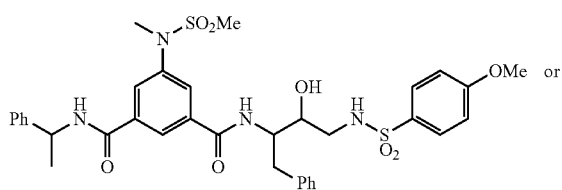

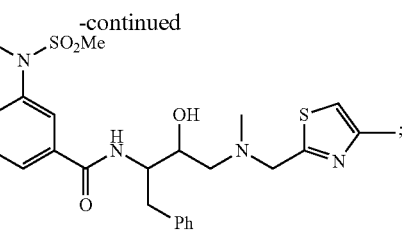

and providing that when $L^3$ is C(O), $R^{4A}$ is aryl, or heteroaryl, each of which is optionally substituted, or $R^{4A}$ and $R^{3A}$ together with $L^3$ and the attached nitrogen form an optionally substituted heterocycle.

In another illustrative embodiment, a compound of the following Formula III is described.

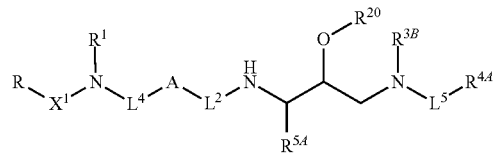

Formula III and solvates, hydrates and pharmaceutically acceptable salts thereof; wherein:

A is a divalent aromatic group;

$R^1$ is hydrogen, alkyl, alkenyl, heteroalkyl, cycloalkyl, heterocyclyl, aryl, arylalkyl, heteroaryl, or heteroarylalkyl, each of which is optionally substituted; and $X^1$ is a bond, alkylene, heteroalkylene, cycloalkylene, or cycloheteroalkylene, each of which is optionally substituted; or $R^1$ and $X^1$ together with the attached nitrogen form an optionally substituted heterocyclyl;

R is hydrogen, alkyl, alkenyl, heteroalkyl, cycloalkyl, heterocyclyl, aryl, arylalkyl, heteroaryl or heteroarylalkyl, each of which is optionally substituted;

$L^4$ is —C(O)—, —S(O)$_n$—, or —CR$^7$R$^{8A}$—; where n is 1 or 2; $R^7$ and $R^{8A}$ are each independently selected from the group consisting of hydrogen, alkyl, alkenyl, heteroalkyl, cycloalkyl, heterocyclyl, aryl, arylalkyl, heteroaryl and heteroarylalkyl, or $R^7$ and $R^{8A}$ together with the carbon atom to which they are attached form an cycloalkyl, each of which is optionally substituted;

$L^2$ is —C(O)— or —S(O)$_p$—, where p is 1 or 2;

$R^{5A}$ is alkyl, alkenyl, heteroalkyl, cycloalkyl, heterocyclyl, aryl, arylalkyl, heteroaryl or heteroarylalkyl, each of which is optionally substituted;

$R^{20}$ is hydrogen or a pro-drug moiety;

$L^5$ is —C(O)—, —S(O)$_q$—, NR$^{9A}$, optionally substituted alkylene, —CH(C(O)NR$^{9A}$R$^{10A}$)—, —CH(C(O)OR$^{9A}$)—, or —CH(S(O)$_r$R$^{9A}$)—; where q is 1 or 2; r is an integer from 0 to 2; and $R^{9A}$ and $R^{10A}$ are each independently selected from the group consisting of hydrogen, alkyl, alkenyl, heteroalkyl, cycloalkyl, heterocyclyl, aryl, arylalkyl, heteroaryl and heteroarylalkyl, each of which is optionally substituted, or $R^{9A}$ and $R^{10A}$ together with the attached nitrogen form an optionally substituted heterocyclyl;

$R^{4A}$ is cycloalkyl, heterocyclyl, aryl, or heteroaryl, each of which is optionally substituted; $R^{3B}$ is hydrogen, alkyl, alkenyl, heteroalkyl, arylalkyl, heteroarylalkyl, heterocyclylalkyl, each of which is optionally substituted, -alkylene-SR$^{11A}$—, alkylene-OR$^{11A}$ or -alkylene-NR$^{11A}$R$^{12A}$, where $R^{11A}$ and $R^{12A}$ are each independently selected from the group consisting of hydrogen, alkyl, alkenyl, heteroalkyl, cycloalkyl, heterocyclyl, aryl, arylalkyl, heteroaryl and heteroarylalkyl, each of which is optionally substituted, or $R^{11A}$ and $R^{12A}$ together with the attached nitrogen form an optionally substituted heterocyclyl; or $R^{4A}$ and $R^{3B}$ together with $L^5$ and the attached nitrogen form an optionally substituted heterocycle;

with the proviso that the compound is not

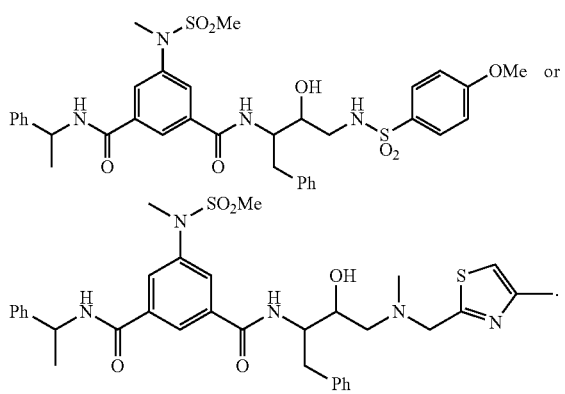

In another illustrative embodiment, a compound of the following Formula V is described.

Formula V

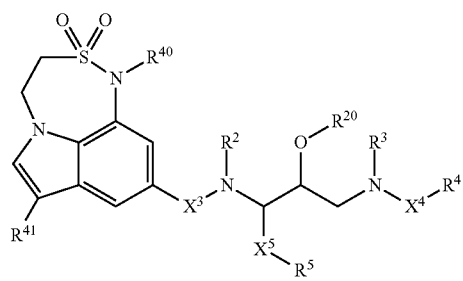

or a pharmaceutically acceptable salt, isomer, mixture of isomers, crystalline form, non crystalline form, hydrate, or solvate thereof; wherein $R^{40}$ is hydrogen, alkyl or heteroalkyl, each of which is optionally substituted;

$R^{41}$ is hydrogen, alkyl or heteroalkyl, each of which is optionally substituted;

$X^3$ is —C(O)— or —S(O)$_p$—;

$X^4$ is a bond, —C(O)—, —S(O)$_q$—, —N(R$^{17}$)—, optionally substituted alkylene, —CH(C(O)R$^{12}$)—, or —CH(S(O)$_n$R$^{11}$)—;

$X^5$ is a bond, —N(R$^{17}$)—, —S(O)$_q$—, or optionally substituted alkylene;

$R^2$ and $R^3$ are each independently selected from the group consisting of hydrogen, —S(O)$_2$R$^{14}$, —C(O)R$^{12}$, —N(R$^8$)R$^9$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; $R^4$ and $R^5$ are each independently selected from the group consisting of hydrogen, halogen, —OH, —NO$_2$, —N(R$^8$)R$^9$, —OR$^{10}$, —S(O)$_n$R$^{11}$, —C(O)R$^{12}$, alkyl, cycloalkyl, heterocycloalkyl, aryl, and heteroaryl, each of which is optionally substituted;

or $R^3$, $R^4$, $X^4$ and the attached nitrogen form an optionally substituted heterocyclyl;

p is independently 1 or 2 in each instance; and q is independently 0, 1, or 2 in each instance;

$R^{20}$ is hydrogen, or a prodrug forming group;

$R^8$ is in each instance independently selected from the group consisting of hydrogen, —C(O)R$^{13}$, —S(O)$_2$R$^{14}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^9$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{10}$ is in each instance independently selected from the group consisting of —C(O)R$^{13}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{11}$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 0; $R^{11}$ is in each instance independently selected from the group consisting of alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 1; and $R^{11}$ is in each instance independently selected from the group consisting of —N(R$^{15}$)R$^{16}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 2;

$R^{12}$ and $R^{13}$ are each independently selected from the group consisting of hydrogen, —OR$^{19}$, —N(R$^{18}$)R$^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{14}$ is in each instance independently selected from the group consisting of hydrogen, —N(R$^{18}$)R$^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; and $R^{15}$, $R^{16}$, $R^{17}$, $R^{18}$, $R^{19}$ are in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted.

In another embodiment, methods for treating AIDS, HIV, and other AIDS-related diseases are described herein, where the method includes the step of administering to a patient in need of relief from the disease a therapeutically effective amount or one or more compounds of Formulae I, II, III and/or V, or a composition containing one or more compounds of Formulae I, II, III and/or V.

In another embodiment, methods for treating AIDS, HIV, and other AIDS-related diseases are described herein, where the method includes the step of administering to a patient in need of relief from the disease a therapeutically effective amount of one or more compounds of Formula IV, or a composition containing one or more compounds of Formula IV

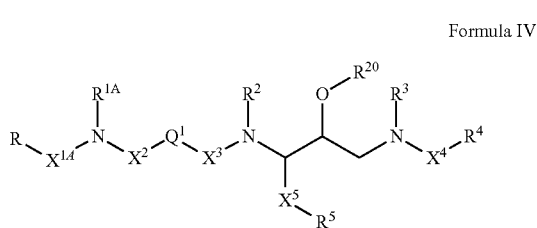

Formula IV or a pharmaceutically acceptable salt, isomer, mixture of isomers, crystalline form, non crystalline form, hydrate, or solvate thereof; wherein R is hydrogen, alkyl, cycloalkyl, heterocycloalkyl, aryl, arylalkyl, heteroaryl, or heteroarylalkyl, each of which is optionally substituted;

$Q^1$ is a cycloalkylene, heterocycloalkylene, arylene, or heteroarylene, each of which is optionally substituted;

$X^{1A}$ is a bond, —N($R^{17}$)—, —S(O)$_q$—, or optionally substituted alkylene; and $R^{1A}$ is —S(O)$_2R^{14}$, —C(O)$R^{12}$, —N($R^8$)$R^9$, alkyl, cycloalkyl, cycloalkyl-alkyl, heterocycloalkyl, heterocycloalkyl-alkyl, aryl, arylalkyl, heteroaryl, or heteroarylalkyl, each of which is optionally substituted, or $R^{1A}$ and $X^{1A}$ together with the attached nitrogen form an optionally substituted heterocyclyl;

$X^2$ is —C(O)—, —S(O)$_n$—, or optionally substituted alkylene;

$X^3$ is —C(O)— or —S(O)$_p$—;

$X^4$ is a bond, —C(O)—, —S(O)$_q$—, —N($R^{17}$)—, optionally substituted alkylene, —CH(C(O)$R^{12}$)—, or —CH(S(O)$_n$$R^{11}$)—;

$X^5$ is a bond, —N($R^{17}$)—, —S(O)$_q$—, or optionally substituted alkylene;

$R^2$ and $R^3$ are each independently selected from the group consisting of hydrogen, —S(O)$_2R^{14}$, —C(O)$R^{12}$, —N($R^8$)$R^9$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; $R^4$ and $R^5$ are each independently selected from the group consisting of hydrogen, halogen, —OH, —NO$_2$, —N($R^8$)$R^9$, —OR$^{10}$, —S(O)$_nR^{11}$, —C(O)$R^{12}$, alkyl, cycloalkyl, heterocycloalkyl, aryl, and heteroaryl, each of which is optionally substituted; or $R^3$, $R^4$, $X^4$ and the attached nitrogen form an optionally substituted heterocyclyl;

p is independently 1 or 2 in each instance; and n and q are each independently 0, 1, or 2 in each instance;

$R^{20}$ is hydrogen, or a prodrug forming group;

$R^8$ is in each instance independently selected from the group consisting of hydrogen, —C(O)$R^{13}$, —S(O)$_2R^{14}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^9$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{10}$ is in each instance independently selected from the group consisting of —C(O)$R^{13}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{11}$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 0; $R^{11}$ is in each instance independently selected from the group consisting of alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 1; and $R^{11}$ is in each instance independently selected from the group consisting of —N($R^{15}$)$R^{16}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 2;

$R^{12}$ and $R^{13}$ are each independently selected from the group consisting of hydrogen, —OR$^{19}$, —N($R^{18}$)$R^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{14}$ is in each instance independently selected from the group consisting of hydrogen, —N($R^{18}$)$R^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; and $R^{15}$, $R^{16}$, $R^{17}$, $R^{18}$, and $R^{19}$ are in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted.

In another embodiment, pharmaceutical compositions comprising one or more compounds of Formulae I, II and/or III are described herein.

In another illustrative embodiment, compounds, pharmaceutical compositions containing such compounds, and methods for using compounds of Formula I are described herein wherein $R^{1A}$ and $X^{1A}$ and the attached nitrogen, and the corresponding groups in each of Formulae II, III, IV, and V, form an optionally substituted heterocyclyl. In another illustrative embodiment, $R^{1A}$ and $X^{1A}$, and the corresponding groups in each of Formulae II, III, IV, and V, and the attached nitrogen form an optionally substituted oxazole. In another illustrative embodiment, $R^{1A}$ and $X^{1A}$, and the corresponding groups in each of Formulae II, III, IV, and V, and the attached nitrogen form an optionally substituted pyrrolidine. In another illustrative embodiment, $R^{1A}$ and $X^{1A}$, and the corresponding groups in each of Formulae II, III, IV, and V, are alkyl and alkylene, respectively.

In another illustrative embodiment, compounds, pharmaceutical compositions containing such compounds, and methods for using compounds of Formula I are described herein wherein $X^2$ and $X^3$, and the corresponding groups in each of Formulae II, III, IV, and V, are —C(O)—.

In another illustrative embodiment, compounds, pharmaceutical compositions containing such compounds, and methods for using compounds of Formula I are described herein wherein $X^4$, and the corresponding group in each of Formulae II, III, IV, and V, is —C(O)— or —S(O)$_2$—, and $R^3$, and the corresponding group in each of Formulae II, III, IV, and V, is alkyl, cycloalkyl, cycloalkyl-alkyl, heterocycloalkyl, heterocycloalkyl-alkyl, aryl, arylalkyl, heteroaryl, or heteroarylalkyl, each of which is optionally substituted. In another illustrative embodiment, $R^3$, and the corresponding group in each of Formulae II, III, IV, and V, $X^4$ and $R^4$, and the corresponding groups in each of Formulae II, III, IV, and V, taken together form optionally substituted arylsulfonyl, such as methoxy, amino, methoxymethyl, and the like phenyl sulfonyl.

In another illustrative embodiment, compounds, pharmaceutical compositions containing such compounds, and methods for using compounds of Formula I are described herein wherein $X^5$, and the corresponding group in each of Formulae II, III, IV, and V, is optionally substituted alkylene. In another illustrative embodiment, $X^5$ and $R^5$, and the corresponding groups in each of Formulae II, III, IV, and V, taken together form optionally substituted arylalkyl, such as benzyl.

In another illustrative embodiment, compounds, pharmaceutical compositions containing such compounds, and methods for using compounds of Formula I are described herein wherein $Q^1$, and the corresponding groups in each of Formulae II, III, and IV is arene or heteroarene, each of which is optionally substituted.

In another illustrative embodiment, compounds, pharmaceutical compositions containing such compounds, and methods for using compounds of Formula I are described herein wherein $X^2$ and $X^3$, and the corresponding groups in each of Formulae II, III, IV, and V, are —C(O)— and $Q^1$ is optionally substituted 1,3-phenylene. In another illustrative embodiment, $X^2$ and $X^3$, and the corresponding groups in each of Formulae II, III, IV, and V, are —C(O)— and $Q^1$ is N-alkyl alkylsulfonylamino, dialkylamino, alkylamino, amino, hydroxy, alkoxy, alkyl, heteroaryl, and like substituted 1,3-phenylene, where the substituent is on C-5. In another illustrative embodiment, $X^2$ and $X^3$, and the corresponding groups in each of Formulae II, III, IV, and V, are —C(O)— and $Q^1$ is optionally substituted 2,4-pyridindiyl or 3,5-pyridindiyl. In another illustrative embodiment, $X^2$ and $X^3$, and the corresponding groups in each of Formulae II, III, IV, and V, are —C(O)— and $Q^1$ is dialkylamino, alkylamino, amino, alkyl, and like substituted 2,4-pyridindiyl, where the substituent is on C-6.

In another illustrative embodiment, compounds, pharmaceutical compositions containing such compounds, and methods for using compounds of Formula I are described herein wherein $R^3$, and the corresponding group in each of Formulae II, III, IV, and V, is $C_3$-$C_{10}$ alkyl or cycloalkyl.

In another illustrative embodiment, compounds, pharmaceutical compositions containing such compounds, and methods for using compounds of Formula I are described herein wherein R, and the corresponding group in each of Formulae II, III, IV, and V, is an optionally substituted aromatic heterocyclyl, such as optionally substituted thiazole. In another illustrative embodiment, R, and the corresponding group in each of Formulae II, III, IV, and V, is optionally substituted oxazole. In another illustrative embodiment, R, and the corresponding group in each of Formulae II, III, IV, and V, is alkyl.

In another illustrative embodiment, compounds, pharmaceutical compositions containing such compounds, and methods for using compounds of Formula I are described herein wherein R and $X^{14}$, and the corresponding groups in each of Formulae II, III, IV, and V, taken together form alkyl, and $R^{14}$, and the corresponding group in each of Formulae II, III, IV, and V, is alkyl. In another illustrative embodiment, R and $X^{14}$, and the corresponding groups in each of Formulae II, III, IV, and V, taken together form alkyl, and $R^{14}$, and the corresponding group in each of Formulae II, III, IV, and V, is hydrogen. In another illustrative embodiment, R and $X^{14}$, and the corresponding groups in each of Formulae II, III, IV, and V, taken together form optionally substituted cycloalkyl, and $R^{14}$, and the corresponding group in each of Formulae II, III, IV, and V, is alkyl. In another illustrative embodiment, R and $X^{14}$, and the corresponding groups in each of Formulae II, III, IV, and V, taken together form optionally substituted heterocycyl, and $R^{14}$, and the corresponding group in each of Formulae II, III, IV, and V, is alkyl. In another illustrative embodiment, R, and the corresponding groups in each of Formulae II, III, IV, and V, is optionally substituted heteroaryl, $X^{14}$, and the corresponding groups in each of Formulae II, III, IV, and V, is alkylene, such as methylene, and $R^{14}$, and the corresponding group in each of Formulae II, III, IV, and V, is alkyl.

In another illustrative embodiment, compounds, pharmaceutical compositions containing such compounds, and methods for using compounds of Formula I are described herein wherein $R^5$, and the corresponding group in each of Formulae II, III, IV, and V, is optionally substituted aryl.

In another illustrative embodiment, compounds, pharmaceutical compositions containing such compounds, and methods for using compounds of Formula I are described herein wherein $X^4$ and $R^4$, and the corresponding groups in each of Formulae II, III, IV, and V, are taken together to form an optionally substituted arylsulphonyl.

In another illustrative embodiment, compounds, pharmaceutical compositions containing such compounds, and methods for using compounds of Formula I are described herein wherein $R^3$, $R^4$ and $X^4$, and the corresponding groups in each of Formulae II, III, IV, and V, are taken together to form a heterocyclyl carboxylic acid or a derivative thereof. In another illustrative embodiment, $R^3$, $R^4$ and $X^4$, and the corresponding groups in each of Formulae II, III, IV, and V, are taken together to form piperazinylcarboxylic acid or a derivative thereof. In another illustrative embodiment, $R^3$, $R^4$ and $X^4$, and the corresponding groups in each of Formulae II, III, IV, and V, are taken together to form perhydroisoquinolinyl carboxylic acid or a derivative thereof.

In another illustrative embodiment, compounds, pharmaceutical compositions containing such compounds, and methods for using compounds of Formula I are described herein wherein $R^3$, and the corresponding group in each of Formulae II, III, IV, and V, is branched alkyl.

In another illustrative embodiment, compounds, pharmaceutical compositions containing such compounds, and methods for using compounds of Formula I are described herein wherein $R^{20}$, and the corresponding group in each of Formulae II, III, IV, and V, is hydrogen.

In another illustrative embodiment, compounds, pharmaceutical compositions containing such compounds, and methods for using compounds of Formula I are described herein wherein $X^5$ and $R^5$, and the corresponding groups in each of Formulae II, III, IV, and V, taken together form an optionally substituted arylalkyl.

In another illustrative embodiment, compounds, pharmaceutical compositions containing such compounds, and methods for using compounds of Formula I are described herein wherein $Q^1$, and the corresponding group in each of Formulae II, III, and IV, is phenylene or pyridinylene, each of which is optionally substituted.

In another illustrative embodiment, compounds, pharmaceutical compositions containing such compounds, and methods for using compounds of Formula I are described herein wherein $X^2$ and $R^{14}$, and the corresponding groups in each of Formulae II, III, IV, and V, are C(O), and hydrogen or alkyl, respectively, and wherein R and $X^{14}$, and the corresponding groups in each of Formulae II, III, IV, and V, are taken together to form an optionally substituted heterocyclylalkyl.

In another illustrative embodiment, compounds, pharmaceutical compositions containing such compounds, and methods for using compounds of Formula I are described herein wherein R, $R^{14}$ and $X^{14}$, and the corresponding groups in each of Formulae II, III, IV, and V, are taken together to form an optionally substituted heterocyclyl.

In another illustrative embodiment, compounds, pharmaceutical compositions containing such compounds, and methods for using compounds of Formula I are described herein wherein $Q^1$, and the corresponding groups in each of Formulae II, III, IV, is a 1,3-phenylene, substituted at the 5-position with an N-alkyl-alkylsulfonamido group.

In another illustrative embodiment, compounds, pharmaceutical compositions containing such compounds, and methods for using compounds of Formula II are described herein wherein W and Z are independently selected from the group of divalent groups consisting of $CR^A$, N, O, $S(O)_m$ and covalently bonded combinations thereof. In another illustrative embodiment, W and Z are each independently selected from the group of divalent groups consisting of N, $CR^A$, and covalently bonded combinations thereof. In another illustrative embodiment, W, Z, and the attached carbons form a six-membered ring. In another illustrative embodiment, W, Z, and the attached carbons form an aromatic ring. In another illustrative embodiment, Z, W, a, b, c and d are taken together to form a phenylene or pyridinylene, each of which is optionally substituted.

In another illustrative embodiment, compounds, pharmaceutical compositions containing such compounds, and methods for using compounds of Formula and III are described herein wherein A is a monocyclic or bicyclic divalent aromatic group. In another illustrative embodiment, A is a divalent phenyl, pyridinyl, pyridazinyl, pyrimidinyl, or pyrazinyl group. In another illustrative embodiment, A is phenylene or pyridinylene, each of which is optionally substituted.

In another illustrative embodiment, compounds, pharmaceutical compositions containing such compounds, and methods for using compounds of Formula II are described herein wherein $L^1$ and $L^2$ are —C(O)—.

In another illustrative embodiment, compounds, pharmaceutical compositions containing such compounds, and methods for using compounds of Formula III are described herein wherein $L^4$ and $L^2$ are —C(O)—.

In another illustrative embodiment, compounds, pharmaceutical compositions containing such compounds, and methods for using compounds of Formula II are described herein wherein $L^3$ is $SO_2$ or C(O).

In another illustrative embodiment, compounds, pharmaceutical compositions containing such compounds, and methods for using compounds of Formula III are described herein wherein $L^5$ is $SO_2$ or C(O).

In another illustrative embodiment, compounds, pharmaceutical compositions containing such compounds, and methods for using compounds of Formula II are described herein wherein $R^{3A}$ is not hydrogen. In another illustrative embodiment, $R^{3A}$ is optionally substituted $C_3$-$C_{10}$ alkyl. In another illustrative embodiment, compounds, pharmaceutical compositions containing such compounds, and methods for using compounds of Formula III are described herein wherein $R^{3B}$ is optionally substituted $C_3$-$C_{10}$ alkyl. In another illustrative embodiment, $R^{3B}$ is not hydrogen.

In another illustrative embodiment, compounds, pharmaceutical compositions containing such compounds, and methods for using compounds of Formula II are described herein wherein $L^3$ is alkylene and $R^{4A}$ is aryl substituted with an oxygen or nitrogen containing substituent. In another illustrative embodiment, $L^5$ is alkylene and $R^{4A}$ is aryl substituted with an oxygen or nitrogen containing substituent. In another illustrative embodiment, $L^3$ is alkylene and $R^{4A}$ is aryl substituted with an oxygen or nitrogen containing substituent, where the substituent is vicinal to $L^3$. In another illustrative embodiment, $L^5$ is alkylene and $R^{4A}$ is aryl substituted with an oxygen or nitrogen containing substituent, where the substituent is vicinal to $L^5$. In another illustrative embodiment, $L^3$ and $R^{4A}$ are taken together to form an optionally substituted arylsulphonyl. In another illustrative embodiment, $L^5$ and $R^{4A}$ are taken together to form an optionally substituted arylsulphonyl.

In another illustrative embodiment, compounds, pharmaceutical compositions containing such compounds, and methods for using compounds of Formula II are described herein wherein $R^{3A}$, $R^{4A}$ and $L^3$ are taken together to form a heterocyclyl carboxylic acid or a derivative thereof. In another illustrative embodiment, compounds, pharmaceutical compositions containing such compounds, and methods for using compounds of Formula III are described herein wherein $R^{3B}$, $R^{4A}$ and $L^5$ are taken together to form a heterocyclyl carboxylic acid or a derivative thereof.

In another illustrative embodiment, compounds, pharmaceutical compositions containing such compounds, and methods for using compounds of Formula II are described herein wherein $R^{3A}$, $R^{4A}$ and $L^3$ are taken together to form piperazinylcarboxylic acid or a derivative thereof. In another illustrative embodiment, compounds, pharmaceutical compositions containing such compounds, and methods for using compounds of Formula III are described herein wherein $R^{3B}$, $R^{4A}$ and $L^5$ are taken together to form piperazinylcarboxylic acid or a derivative thereof.

In another illustrative embodiment, compounds, pharmaceutical compositions containing such compounds, and methods for using compounds of Formula II are described herein wherein $R^{3A}$, $R^{4A}$ and $L^3$ are taken together to form perhydroisoquinolinyl carboxylic acid or a derivative thereof. In another illustrative embodiment, compounds, pharmaceutical compositions containing such compounds, and methods for using compounds of Formula III are described herein wherein $R^{3B}$, $R^{4A}$ and $L^5$ are taken together to form perhydroisoquinolinyl carboxylic acid or a derivative thereof.

In another illustrative embodiment, compounds, pharmaceutical compositions containing such compounds, and methods for using compounds of Formula II are described herein wherein $R^{3A}$ is branched alkyl. In another illustrative embodiment, compounds, pharmaceutical compositions containing such compounds, and methods for using compounds of Formula III are described herein wherein $R^{3B}$ is branched alkyl.

In another illustrative embodiment, compounds, pharmaceutical compositions containing such compounds, and methods for using compounds of Formula II are described herein wherein $R^{20}$ is hydrogen. In another illustrative embodiment, compounds, pharmaceutical compositions containing such compounds, and methods for using compounds of Formula III are described herein wherein $R^{20}$ is hydrogen.

In another illustrative embodiment, compounds, pharmaceutical compositions containing such compounds, and methods for using compounds of Formula I are described herein wherein $R^{5A}$, and the corresponding group in each of Formulae II, III, IV, and V, is optionally substituted arylalkyl. In another illustrative embodiment, compounds, pharmaceutical compositions containing such compounds, and methods for using compounds of Formula III are described herein wherein $R^{5A}$ is optionally substituted arylalkyl.

In another illustrative embodiment, compounds, pharmaceutical compositions containing such compounds, and methods for using compounds of Formula II are described herein wherein $L^1$ is C(O), $R^1$ is hydrogen or alkyl, and R and $X^1$ are taken together to form an optionally substituted heterocyclylalkyl. In another illustrative embodiment, compounds, pharmaceutical compositions containing such compounds, and methods for using compounds of Formula III are described herein wherein $L^4$ is C(O), $R^1$ is hydrogen or alkyl, and R and $X^1$ are taken together to form an optionally substituted heterocyclylalkyl In another illustrative embodiment, compounds, pharmaceutical compositions containing such compounds, and methods for using compounds of Formulae II and III are described herein wherein R, $R^1$ and $X^1$ are taken together to form an optionally substituted heterocyclyl.

In another illustrative embodiment, compounds, pharmaceutical compositions containing such compounds, and methods for using compounds of Formula V are described herein wherein $X^3$ is —C(O)—, $R^{40}$ is alkyl, and $R^{41}$ is alkyl.

In another illustrative embodiment, compounds, pharmaceutical compositions containing such compounds, and methods for using compounds of Formula V are described herein wherein $X^3$ is —C(O)—, $R^{40}$ is methyl and $R^{41}$ is ethyl.

In another illustrative embodiment, the methods described herein include compounds, and pharmaceutical compositions containing such compounds of the following formulae

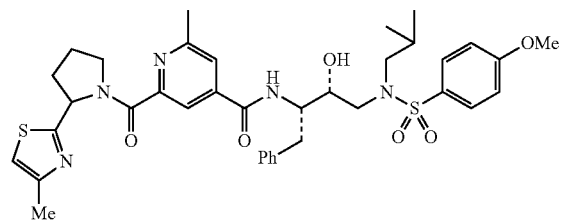

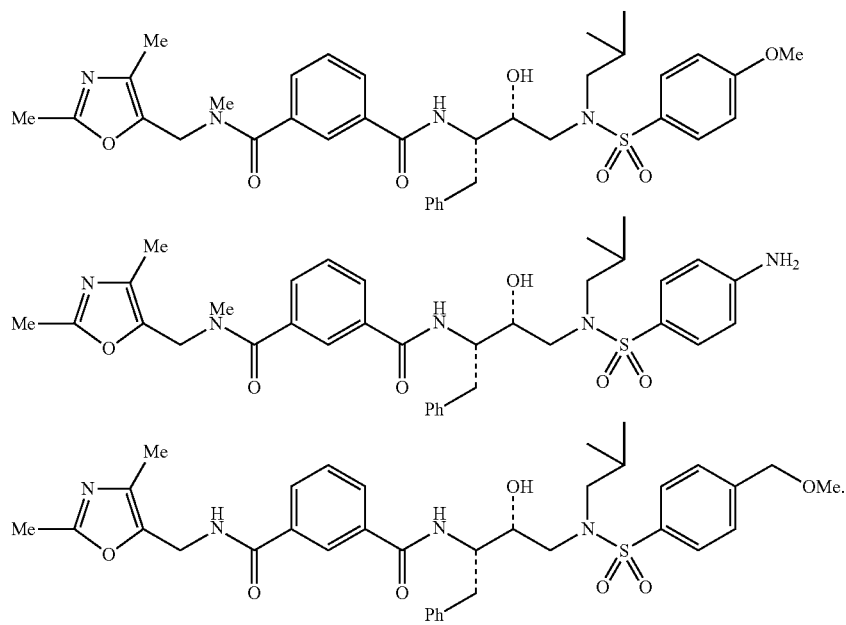

In one illustrative embodiment, the methods described herein include compounds, and pharmaceutical compositions containing such compounds of the following formulae

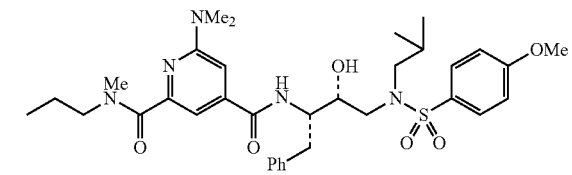

In another illustrative embodiment, the methods described herein include compounds, and pharmaceutical compositions containing such compounds of the following formulae

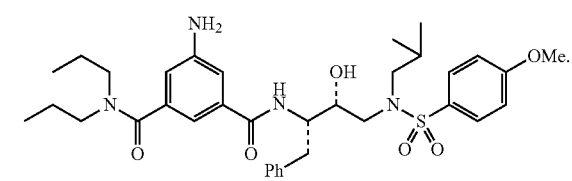

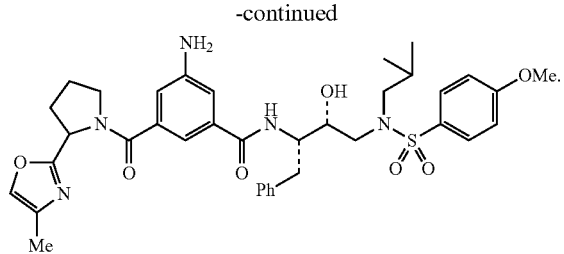

In another illustrative embodiment, the methods described herein include compounds, and pharmaceutical compositions containing such compounds of the following formulae

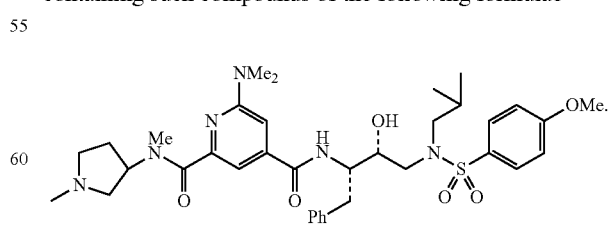

In another illustrative embodiment, the methods described herein include compounds, and pharmaceutical compositions containing such compounds of the following formulae

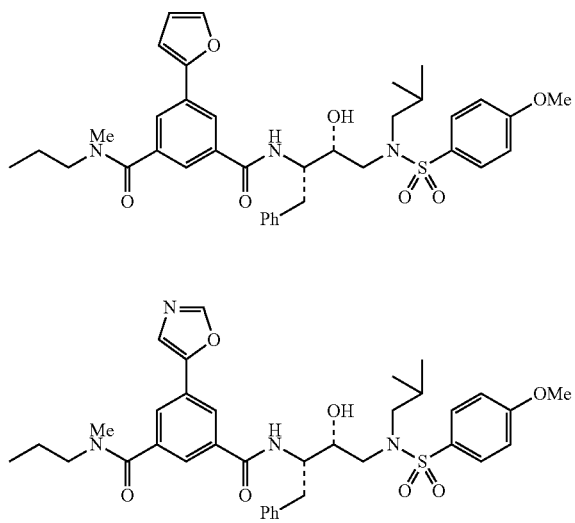
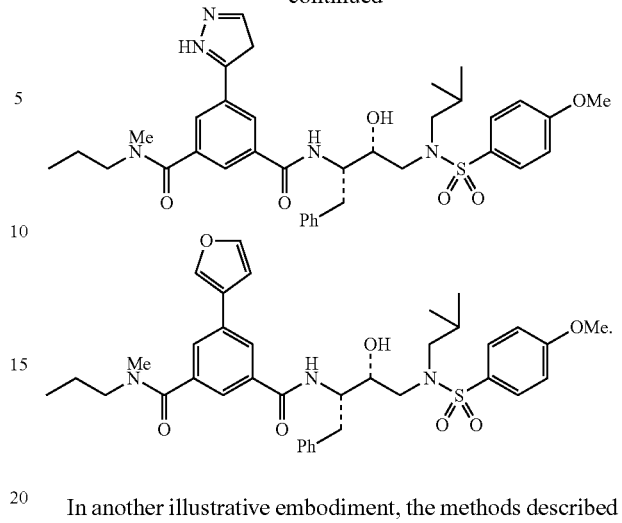
In another illustrative embodiment, the methods described herein include compounds, and pharmaceutical compositions containing such compounds of the following formulae
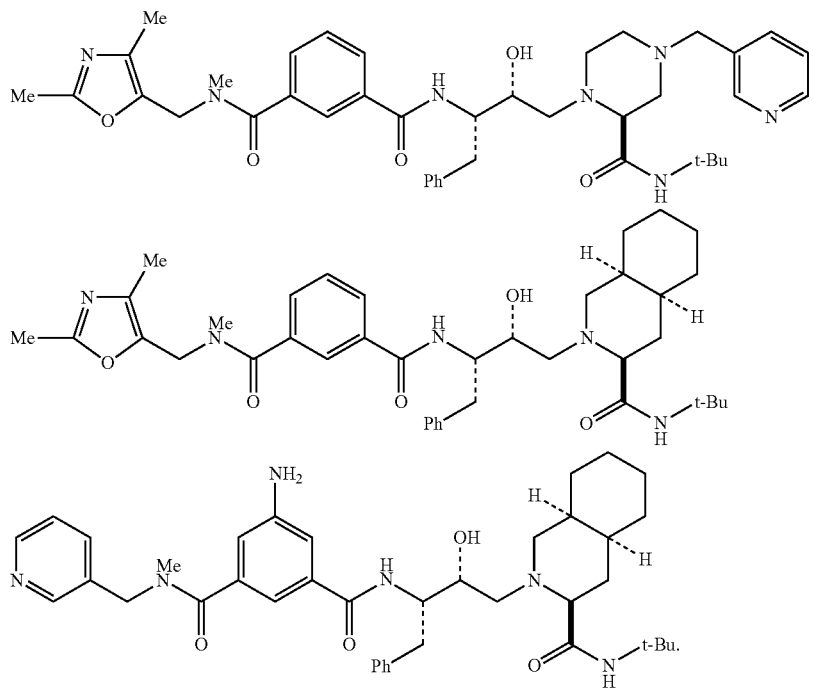
In another illustrative embodiment, the methods described herein include compounds, and pharmaceutical compositions containing such compounds of the following formulae
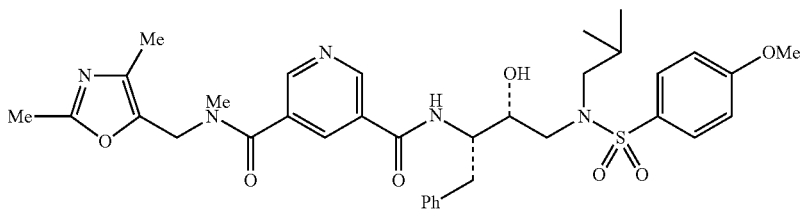

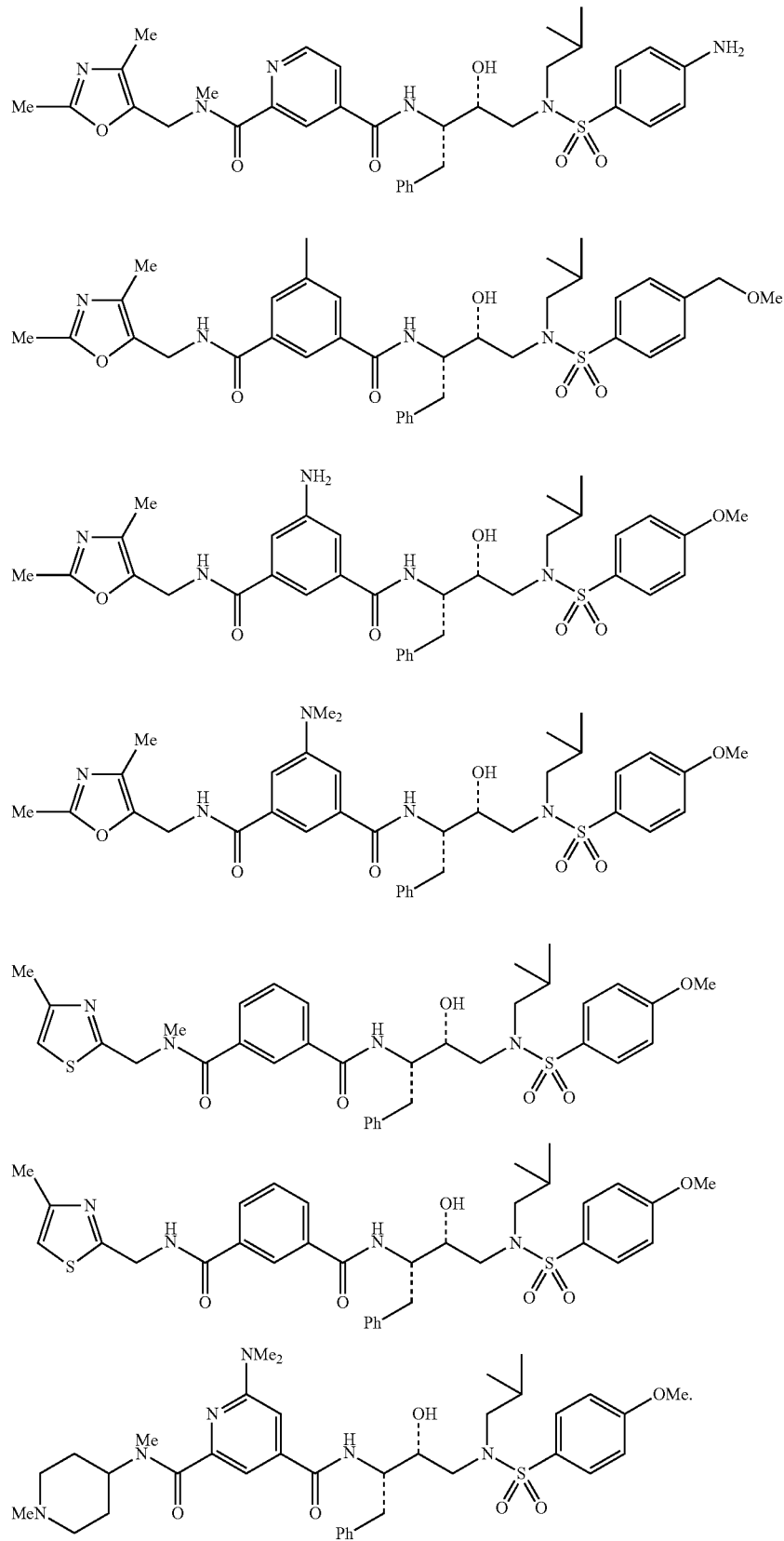

In another illustrative embodiment, the methods described herein include compounds, and pharmaceutical compositions containing such compounds of the following formulae

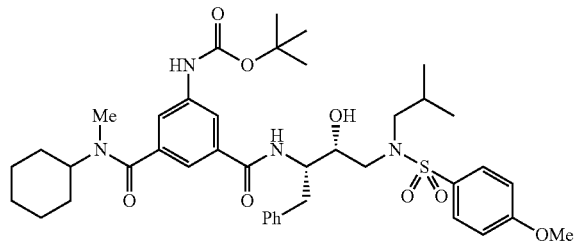

C$_{41}$H$_{56}$N$_4$O$_8$S
Mol. Wt.: 764.9703

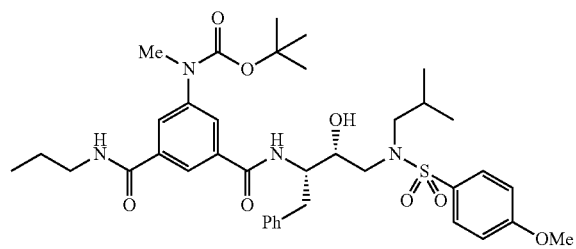

C$_{38}$H$_{52}$N$_4$O$_8$S
Mol. Wt.: 724.9065

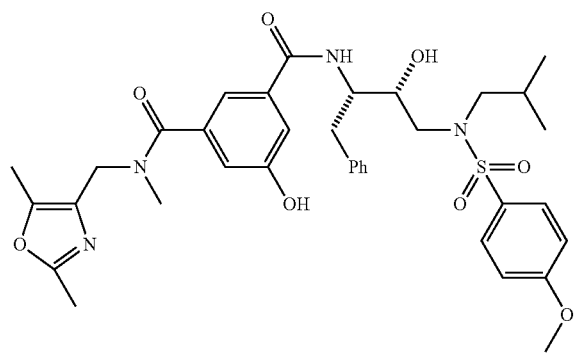

C$_{36}$H$_{44}$N$_4$O$_8$S
Mol. Wt.: 692.8216

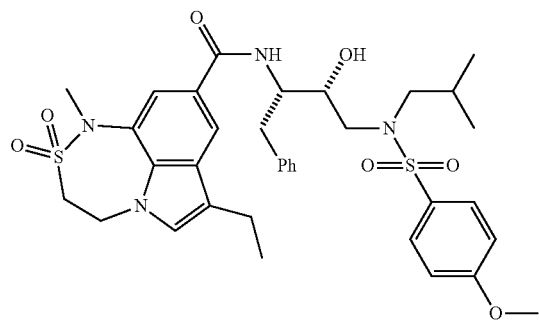

C$_{35}$H$_{44}$N$_4$O$_7$S$_2$
Mol. Wt.: 696.8765

-continued

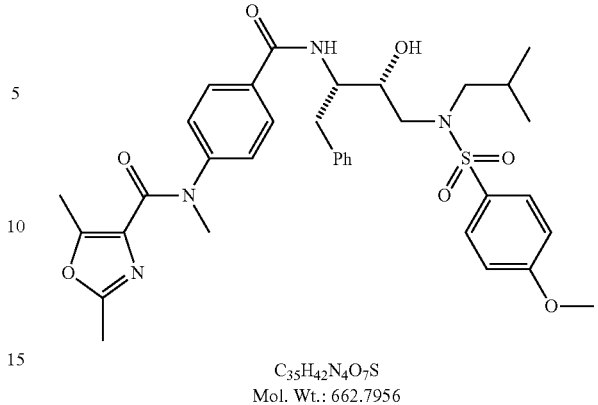

C$_{35}$H$_{42}$N$_4$O$_7$S
Mol. Wt.: 662.7956

In another illustrative embodiment, compounds that inhibit HIV protease are described. Illustrative examples of such compounds are shown in TABLE 1.

In another embodiment, pharmaceutical dosage forms of and methods of administration of the compounds are described herein. The compounds described herein can be prepared and administered in a wide variety of conventional oral, parenteral and topical dosage forms, utilizing art-recognized products. See generally, Remington: The Science and Practice of Pharmacy, (21$^{st}$ ed., 2005). Thus, the compounds described herein can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds described herein can be administered transdermally. It is also envisioned that multiple routes of administration (e.g., intramuscular, oral, transdermal) can be used to administer the compounds described herein. Accordingly, pharmaceutical compositions comprising a pharmaceutically acceptable carrier or excipient and one or more compounds described herein are described.

In making the formulations of the compounds described herein, a therapeutically effective amount of the inhibitor in any of the various forms described herein may be mixed with an excipient, diluted by an excipient, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), soft and hard gelatin capsules, suppositories, sterile injectable solutions, and sterile packaged powders. The compositions may contain anywhere from about 0.1% to about 99.9% active ingredients, depending upon the selected dose and dosage form. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (Generally Regarded as Safe) compounds.

The compounds described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The compounds described herein may be capable of existing as geometric isomers. Accordingly, it is to be understood that the present invention includes pure geometric isomers or mixtures of geometric isomers.

In this and other embodiments described herein, it is understood that the compounds may be neutral or may be one or more pharmaceutically acceptable salts, crystalline forms, non crystalline forms, hydrates, or solvates, or a combination of the foregoing. Accordingly, all references to the compounds described herein may refer to the neutral molecule, and/or those additional forms thereof collectively and individually from the context.

The term "cycloalkyl" as used herein includes molecular fragments or radicals comprising a bivalent chain of carbon atoms, at least a portion of which forms a ring. It is to be understood that the term cycloalkyl as used herein includes fragments and radicals attached at either ring atoms or non-ring atoms, such as cyclopropyl, cyclohexyl, 3-ethylcyclopent-1-yl, cyclopropylethyl, cyclohexylmethyl, and the like.

The term "cycloalkenyl" as used herein generally refers to a monovalent chain of carbon atoms containing one or more unsaturated bonds, at least a portion of which forms a ring.

The term "cycloalkylene" as used herein includes molecular fragments or radicals comprising a bivalent chain of carbon atoms, a portion of which forms a ring. It is to be understood that the term cycloalkyl as used herein includes fragments and radicals attached at either ring atoms or non-ring atoms, such as cycloprop-1,1-diyl, cycloprop-1,2-diyl, cyclohex-1,4-diyl, 3-ethylcyclopent-1,2-diyl, 1-methylenecyclohex-4-yl, and the like.

The terms "heteroalkyl" and "heteroalkylene" as used herein includes molecular fragments or radicals comprising monovalent and divalent, respectively, groups that are formed from a linear or branched chain of carbon atoms and heteroatoms, wherein the heteroatoms are selected from nitrogen, oxygen, and sulfur, such as alkoxyalkyl, alkyleneoxyalkyl, aminoalkyl, alkylaminoalkyl, alkyleneaminoalkyl, alkylthioalkyl, alkylenethioalkyl, alkoxyalkylaminoalkyl, alkylaminoalkoxyalkyl, alkyleneoxyalkylaminoalkyl, and the like. It is to be understood that neither heteroalkyl nor heteroalkylene includes oxygen-oxygen fragments. It is also to be understood that neither heteroalkyl nor heteroalkylene includes oxygen-sulfur fragments, unless the sulfur is oxidized as $S(O)$ or $S(O)_2$.

As used herein, the term "haloalkyl" generally refers to an alkyl group wherein one or more hydrogen atoms is replaced with a halogen atom, independently selected in each instance from the group consisting of fluorine, chlorine, bromine and iodine. Non-limiting, illustrative examples include, difluoromethly, 2,2,2-trifluoroethyl, 2-chlorobutyl, 2-chloro-2-propyl, trifluoromethyl, bromodifluoromethyl, and the like.

The terms "heterocycle" and "heterocycloalkylene" as used herein include molecular fragments or radicals comprising a monovalent or divalent chain of carbon atoms and heteroatoms, respectively, wherein the heteroatoms are selected from nitrogen, oxygen, and sulfur, at least a portion of which, including at least one heteroatom, form a ring, such as aziridine, pyrrolidine, oxazolidine, 3-methoxypyrrolidine, 3-methylpiperazine, and the like, and wherein the fragment or radical may contain one or more unstaturated bonds. Accordingly, as used herein, heterocycle includes alkylheterocycle, heteroalkylheterocycle, heterocyclylalkyl, heterocyclylheteroalkyl, and the like. It is to be understood that the term heterocycle as used herein includes fragments and radicals attached at either ring atoms or non-ring atoms, such as tetrahydrofuran-2-yl, piperidin-1-yl, piperidin-4-yl, piperazin-1-yl, morpholin-1-yl, tetrahydrofuran-2-ylmethyl, piperidin-1-ylethyl, piperidin-4-ylmethyl, piperazin-1-ylpropyl, morpholin-1-ylethyl, and the like. It is also understood that The term "aryl" as used herein includes molecular fragments or radicals comprising an aromatic mono or polycyclic ring of carbon atoms, such as phenyl, naphthyl, and the like.

The term "heteroaryl" as used herein includes molecular fragments or radicals comprising an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term "substituted aryl" or "substituted heteroaryl" as used herein includes molecular fragments or radicals comprising aryl or heteroaryl substituted with one or more substituents, such as alkyl, heteroalkyl, halo, hydroxy, amino, alkyl or dialkylamino, alkoxy, alkylsulfonyl, aminosulfonyl, carboxylate, alkoxycarbonyl, aminocarbonyl, cyano, nitro, and the like. It is to be understood that the alkyl groups in such substituents may be optionally substituted with halo.

It is also appreciated that in the foregoing embodiments, certain aspects of the compounds are presented in the alternative, such as selections for any one or more of R, $R^A$, $Q^1$, W, Z, $X^1$, $X^{1A}$, $X^2$, $X^3$, $X^4$, $X^5$, $L^1$, $L^2$, $L^3$, $L^4$, $L^5$, A, $R^1$, $R^{1A}$, $R^2$, $R^3$, $R^{3A}$, $R^{3B}$, $R^4$, $R^5$, $R^{4A}$, $R^{5A}$, $R^6$, $R^7$, $R^8$, $R^{8A}$, $R^9$, $R^{10}$, $R^{11}$, $R^{12}$, $R^{13}$, $R^{14}$, $R^{9A}$, $R^{10A}$, $R^{11A}$, $R^{12A}$, $R^{13A}$, $R^{14A}$, $R^{15}$, $R^{16}$, $R^{17}$, $R^{18}$, $R^{19}$, $R^{20}$, a, b, c, d, n, m, p, q, and r. It is therefore to be understood that various alternate embodiments of the invention include individual members of those lists, as well as the various subsets of those lists. Each of those combinations is to be understood to be described herein by way of the lists. For example, in such alternative embodiments, compounds of Formula I are described wherein R is a substituted heteroaryl, $X^{1A}$ is alkylene, $Q^1$ is a 1,3-phenylene, and each of $X^2$ and $X^3$ is C(O).

The examples described herein are to be construed as illustrative only and are not meant to limit the scope of compounds or compositions that are contemplated in the present invention and a skilled person will readily recognize additional compounds that fall within the scope of the present invention.

METHODS AND EXAMPLES

Example 1

Synthesis

The compounds herein contemplated are synthesized by an appropriate combination of generally well known synthetic methods. Techniques useful in synthesizing the compounds described herein are both readily apparent and accessible to those of skill in the relevant art. The discussion below is offered to illustrate certain of the diverse methods available for use in assembling the compounds described herein. However, the discussion is not intended to define the scope of reactions or reaction sequences that are useful in preparing the compounds described herein.

In an illustrative example, inhibitors described herein are synthesized using the route shown in the following scheme. Other examples can be prepared using routine modifications, known to those skilled in the art of organic synthesis, of the schemes shown herein.

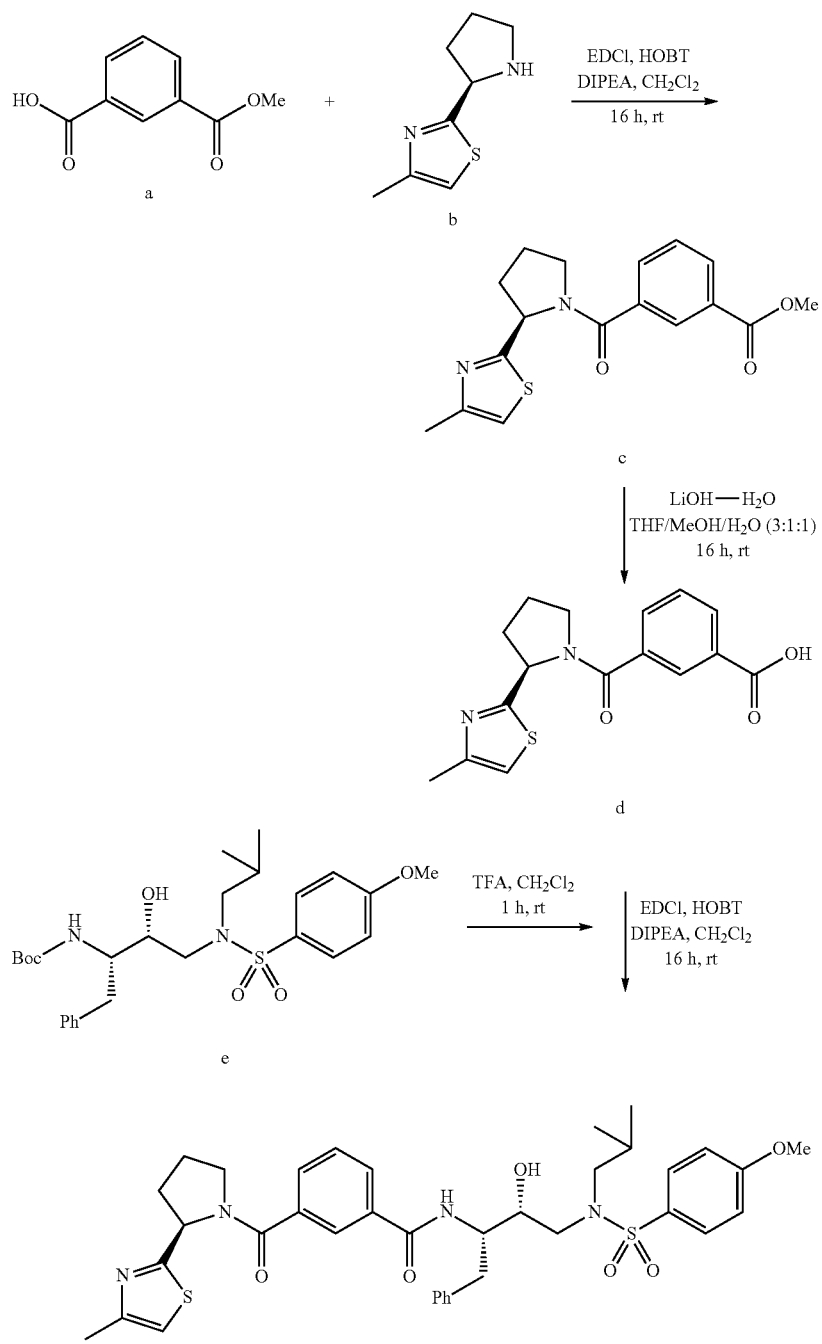
In another embodiment, compounds of formula I, wherein $X^2$ and $X^3$ are —C(O)— and $R^{20}$ is hydrogen are synthesized as shown below.
-continued
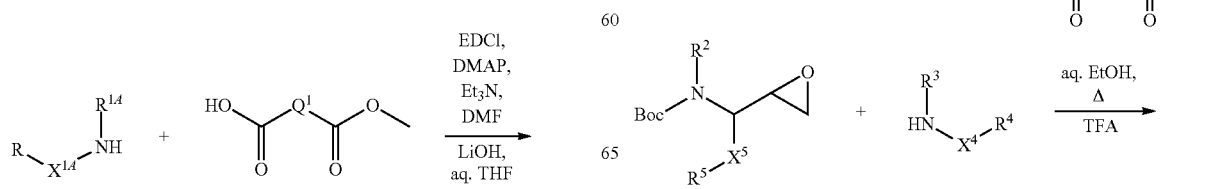

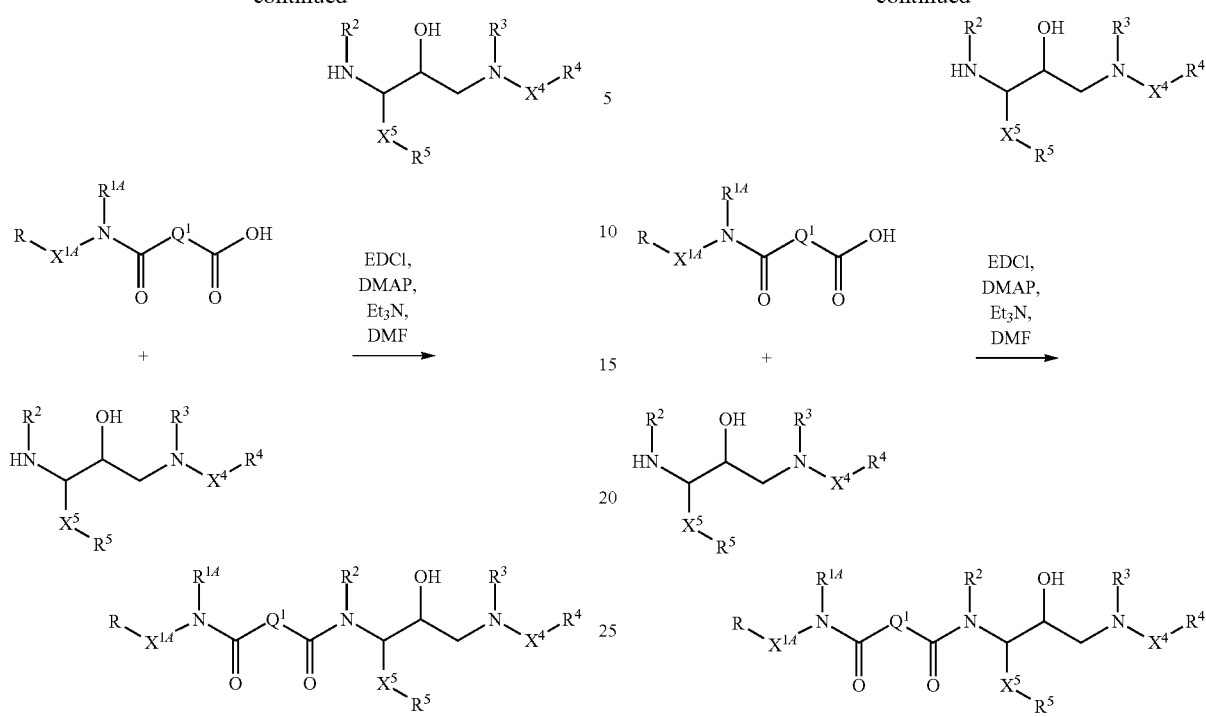
In another embodiment, compounds of formula I, wherein $X^2$ and $X^3$ are —C(O)— and $R^{20}$ is hydrogen are synthesized as shown below.
In another embodiment, compounds of formula II, wherein $L^1$ and $L^2$ are —C(O)— and $R^{20}$ is hydrogen are synthesized as shown below.
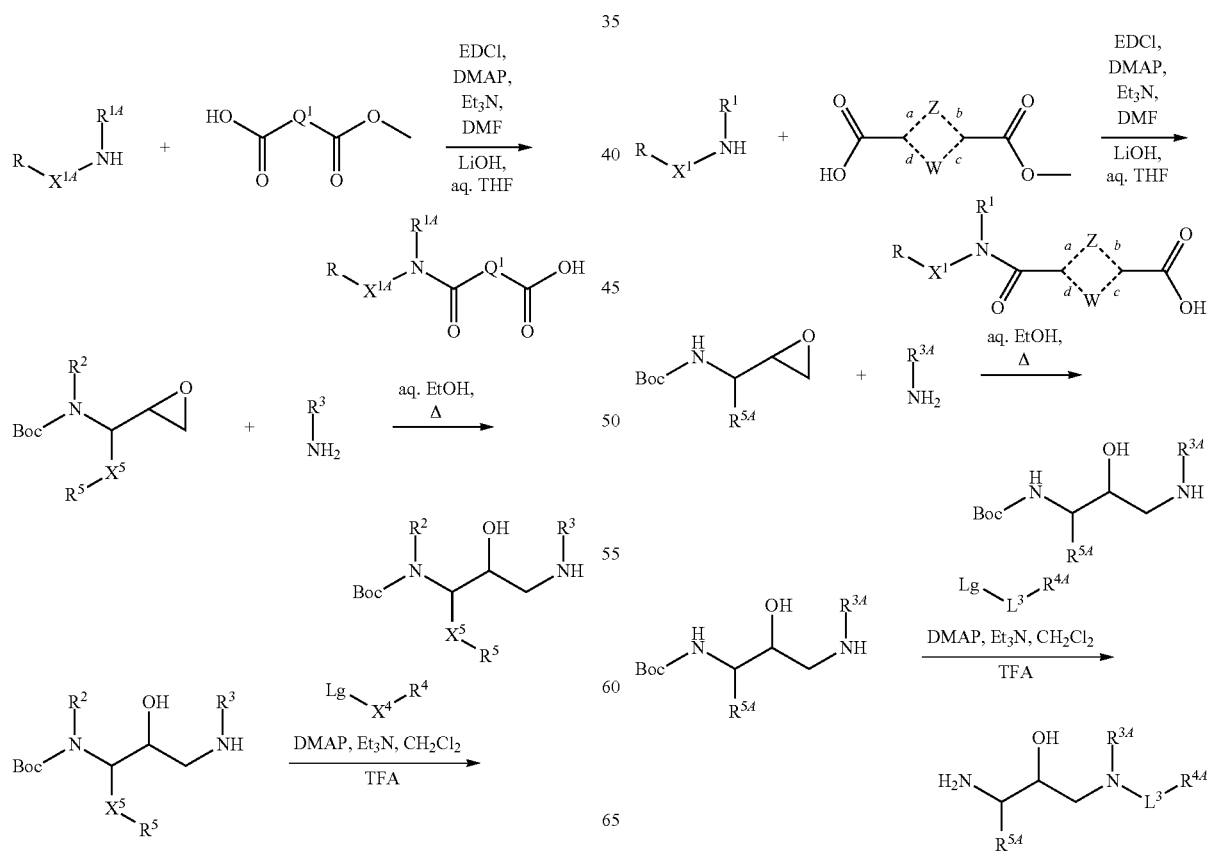

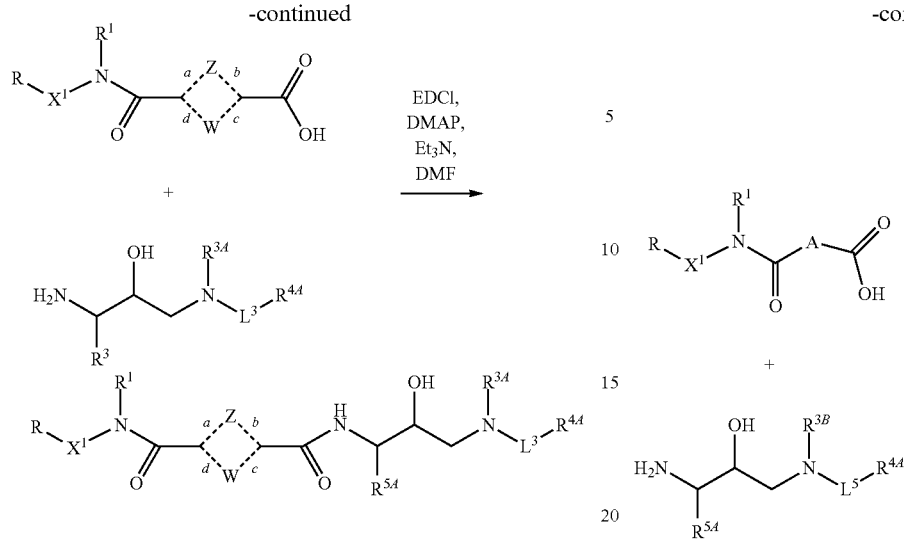

In another embodiment, compounds of formula III, wherein $L^4$ and $L^2$ are —C(O)— and $R^{20}$ is hydrogen are synthesized as shown below.

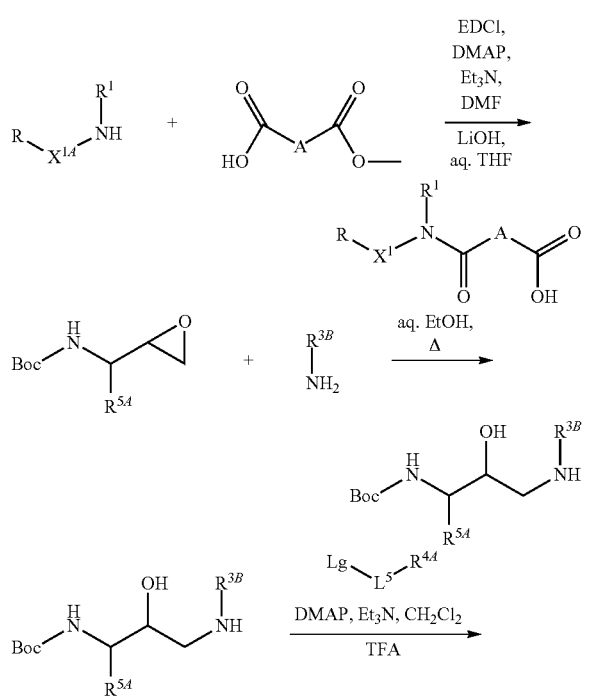

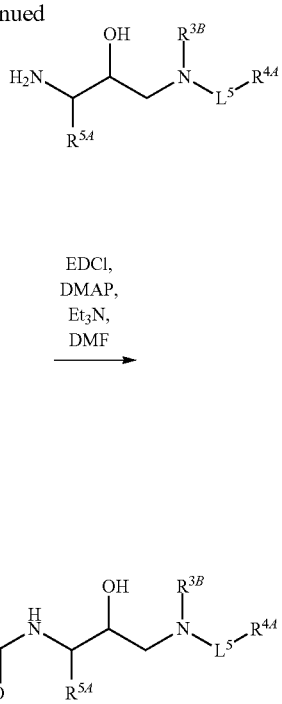

Example 2

Inhibition of HIV Proteases

Without being bound by theory, it is suggested that the compounds described herein may exert their utility by the inhibition of proteases encoded by human immunodeficiency virus. Techniques for measurement of the ability of the compounds herein described to decrease the proteolytic activity of proteases encoded by HIV are well known to those skilled in the relevant art and any one or combination of such techniques can be used to measure the inhibition of protease activity of the compound herein described. One illustrative method is described by Toth and Marshall (Toth & Marshall, *Int. J. Pep. Protein Res.* (1990), 36, 544-550). The disclosure of the foregoing is incorporated herein in its entirety by reference. In addition, the entirety of the disclosures of each of the publications cited herein are also incorporated herein by reference. Measured inhibition constants are shown in TABLE 1.

TABLE 1

| Compound | Inhibition of HIV-1 ($K_i$) | Inhibition of HIV-1 ($IC_{50}$) |
|---|---|---|
| | 0.6 nM | |

TABLE 1-continued
| Compound | Inhibition of HIV-1 ($K_i$) | Inhibition of HIV-1 ($IC_{50}$) |
| --- | --- | --- |
| 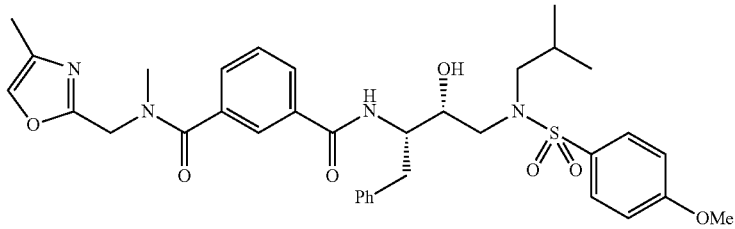<br>$C_{35}H_{42}N_4O_7S$<br>Mol. Wt.: 662.7956 | 0.6 nM | 0.02 µM |
| 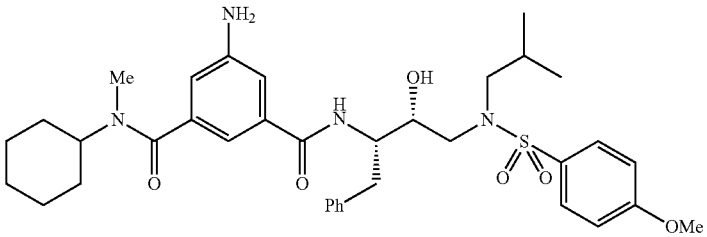<br>$C_{36}H_{48}N_4O_6S$<br>Mol. Wt.: 664.8545 | 300 nM | |
| 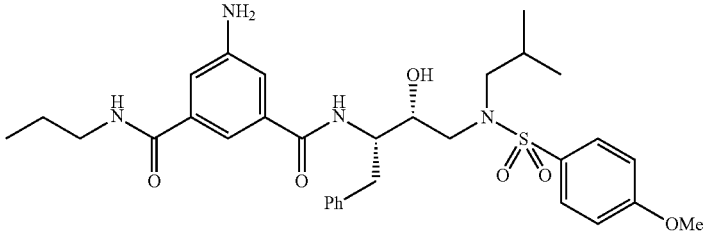<br>$C_{32}H_{42}N_4O_6S$<br>Mol. Wt.: 610.7641 | 400 nM | |
| 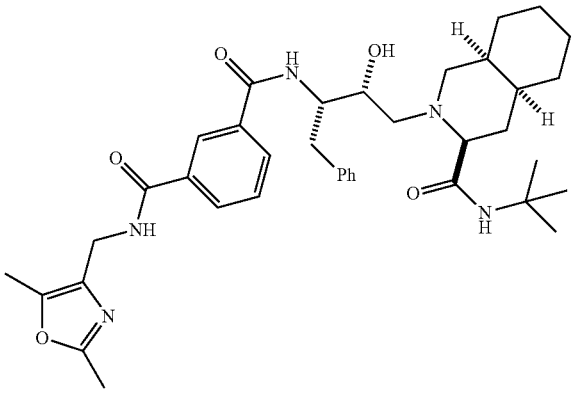 [SMILES: Cc1nc(CN(C)C(=O)c2cccc(C(=O)N[C@@H](Cc3ccccc3)[C@H](O)CN3C[C@H]4CCCC[C@H]4C[C@H]3C(=O)NC(C)(C)C)c2)c(C)o1]<br>$C_{38}H_{51}N_5O_5$<br>Mol. Wt.: 657.8420 | 20 nM | |

TABLE 1-continued
| Compound | Inhibition of HIV-1 ($K_i$) | Inhibition of HIV-1 ($IC_{50}$) |
|---|---|---|
| 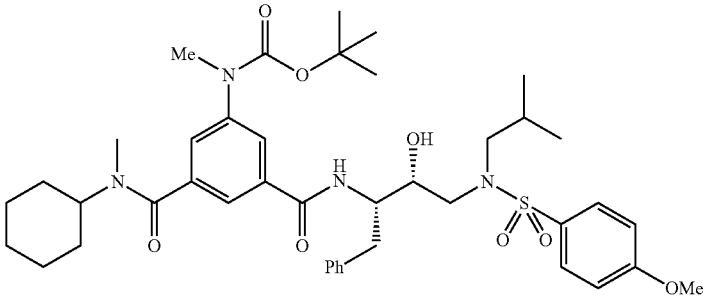<br>$C_{42}H_{58}N_4O_8S$<br>Mol. Wt.: 778.9969 | | 1000 nM |
| 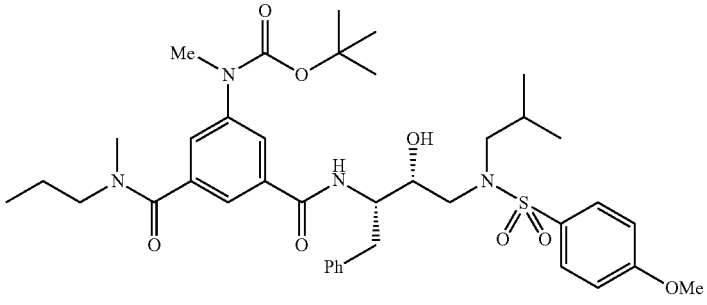<br>$C_{39}H_{54}N_4O_8S$<br>Mol. Wt.: 738.9331 | | 1000 nM |
| 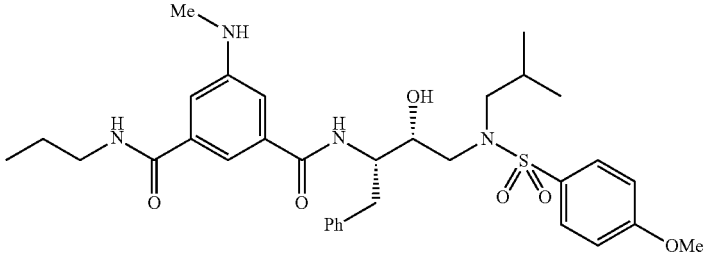<br>$C_{33}H_{44}N_4O_6S$<br>Mol. Wt.: 624.7907 | | 300 nM |
| 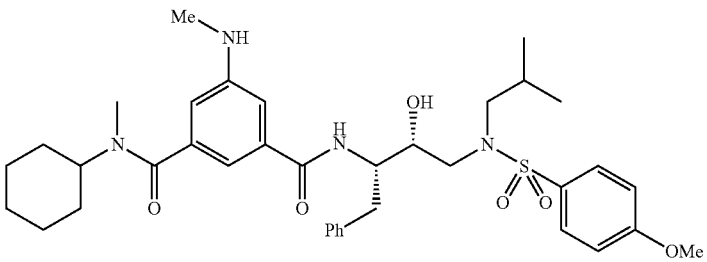<br>$C_{37}H_{50}N_4O_6S$<br>Mol. Wt.: 678.8811 | | 200 nM |

TABLE 1-continued

| Compound | Inhibition of HIV-1 ($K_i$) | Inhibition of HIV-1 ($IC_{50}$) |
|---|---|---|
| $C_{34}H_{46}N_4O_6S$  Mol. Wt.: 638.8172 | | 200 nM |
| $C_{37}H_{49}N_3O_7S$  Mol. Wt.: 679.8659 | | 40 nM |
| $C_{33}H_{43}N_3O_7S$  Mol. Wt.: 625.7754 | | 50 nM |
| (structure) | | 5 nM |

TABLE 1-continued

| Compound | Inhibition of HIV-1 ($K_i$) | Inhibition of HIV-1 ($IC_{50}$) |
|---|---|---|
| [structure] | | 100 nM |
| [structure] | | 20 nM |
| [structure] | | 200 nM |
| [structure] $C_{34}H_{45}N_3O_7S$ Mol. Wt.: 639.8020 | | 20 nM |

TABLE 1-continued
| Compound | Inhibition of HIV-1 ($K_i$) | Inhibition of HIV-1 ($IC_{50}$) |
|---|---|---|
| 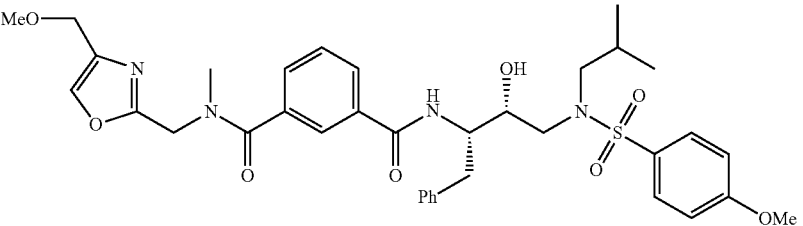<br>$C_{36}H_{44}N_4O_8S$<br>Mol. Wt.: 692.8216 | 0.3 nM | |
| 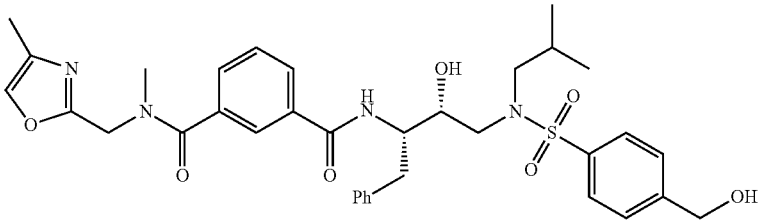<br>$C_{35}H_{42}N_4O_7S$<br>Mol. Wt.: 662.7956 | 0.6 nM | |
| 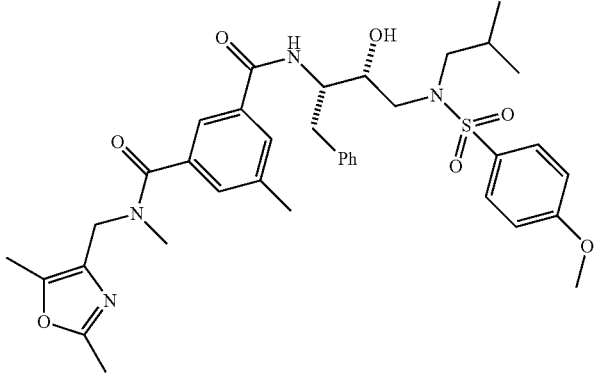 [SMILES: COc1ccc(S(=O)(=O)N(CC(C)C)C[C@@H](O)[C@H](Cc2ccccc2)NC(=O)c2cc(C)cc(C(=O)N(C)Cc3nc(C)oc3C)c2)cc1] | 0.2 nM | 0.03 μM |
| 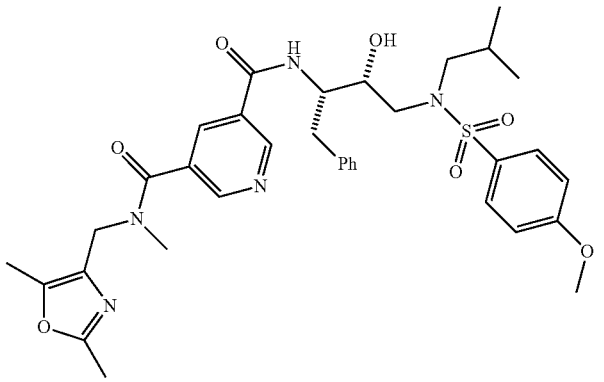 [SMILES: COc1ccc(S(=O)(=O)N(CC(C)C)C[C@@H](O)[C@H](Cc2ccccc2)NC(=O)c2cncc(C(=O)N(C)Cc3nc(C)oc3C)c2)cc1] | 6 nM | |

TABLE 1-continued

| Compound | Inhibition of HIV-1 ($K_i$) | Inhibition of HIV-1 ($IC_{50}$) |
|---|---|---|
| (structure) | 1 nM | |
| (structure) | 5 nM | |
| (structure) | 70 nM | |
| (structure) | 100 nM | |

TABLE 1-continued
| Compound | Inhibition of HIV-1 ($K_i$) | Inhibition of HIV-1 ($IC_{50}$) |
|---|---|---|
| 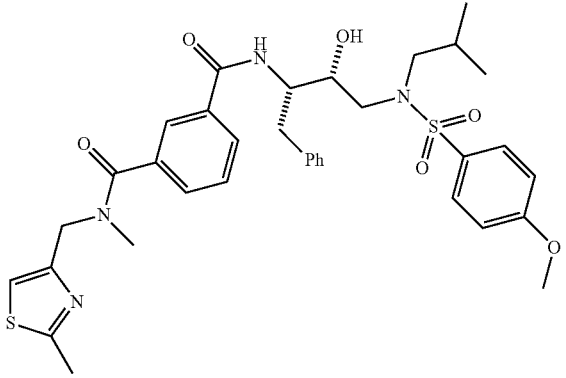 [SMILES: COc1ccc(S(=O)(=O)N(CC(C)C)C[C@@H](O)[C@H](Cc2ccccc2)NC(=O)c2cccc(C(=O)N(C)Cc3csc(C)n3)c2)cc1] | | 0.1 nM |
| 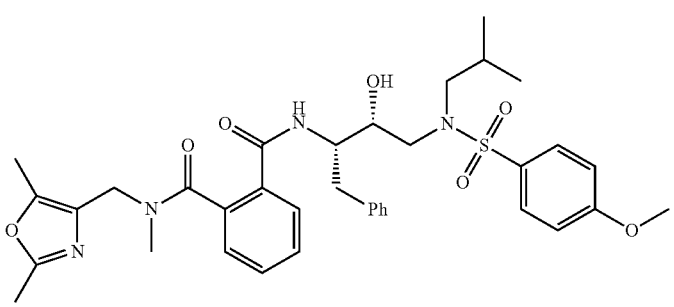 [SMILES: COc1ccc(S(=O)(=O)N(CC(C)C)C[C@@H](O)[C@H](Cc2ccccc2)NC(=O)c2ccccc2C(=O)N(C)Cc2nc(C)oc2C)cc1] | | 600 nM |
| 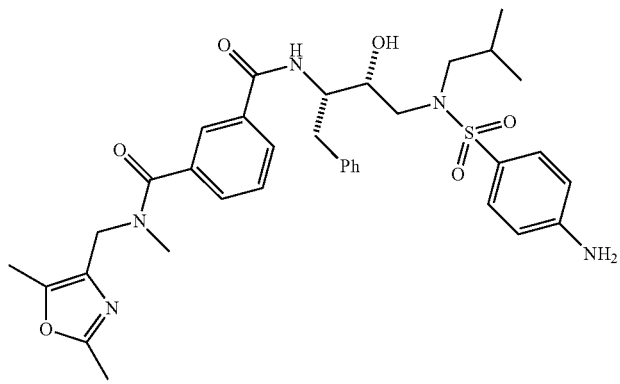 [SMILES: Cc1nc(CN(C)C(=O)c2cccc(C(=O)N[C@@H](Cc3ccccc3)[C@H](O)CN(CC(C)C)S(=O)(=O)c3ccc(N)cc3)c2)c(C)o1] | | 2 nM |
| 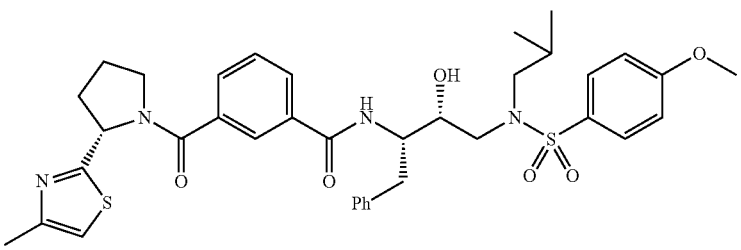<br>$C_{37}H_{44}N_4O_6S_2$<br>Mol. Wt.: 704.8985 | | 30 nM |

TABLE 1-continued

| Compound | Inhibition of HIV-1 ($K_i$) | Inhibition of HIV-1 ($IC_{50}$) |
|---|---|---|
| 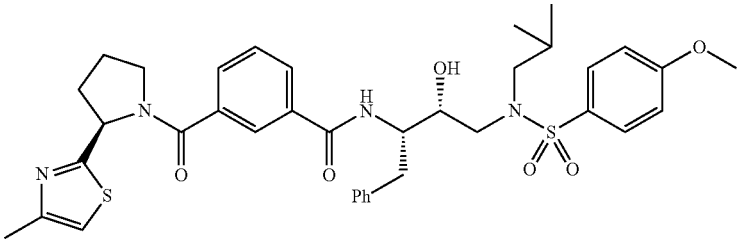
$C_{37}H_{44}N_4O_6S_2$
Mol. Wt.: 704.8985 | 0.03-08 nM | 32 nM |

What is claimed is:

1. A compound of the formula

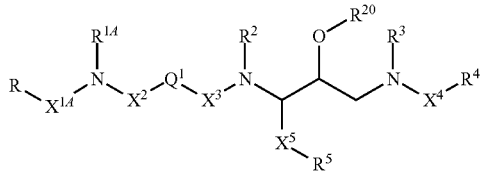

or a pharmaceutically acceptable salt thereof; wherein

R is hydrogen, alkyl, cycloalkyl, heterocycloalkyl, aryl, arylalkyl, heteroaryl, or heteroarylalkyl, each of which is optionally substituted;

$X^2$ and $X^3$ are —C(O)—;

$Q^1$ is optionally substituted 1,3-phenylene;

$R^{1A}$ and $X^{1A}$ together with the attached nitrogen an optionally substituted heterocycle or R, $R^{1A}$ and $X^{1A}$ and the attached nitrogen are taken together to form an optionally substituted heterocycle;

$X^4$ is —C(O)— or —S(O)$_2$—;

$R^3$ is alkyl, cycloalkyl, cycloalkyl-alkyl, heterocycloalkyl, heterocycloalkyl-alkyl, aryl, arylalkyl, heteroaryl, or heteroarylalkyl, each of which is optionally substituted;

$X^5$ is optionally substituted alkylene;

$R^2$ is selected from the group consisting of hydrogen, —S(O)$_2$R$^{14}$, —C(O)R$^{12}$, —N(R$^8$)R$^9$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^4$ and $R^5$ are each independently selected from the group consisting of hydrogen, halogen, —OH, —NO$_2$, —N(R$^8$)R$^9$, —OR$^{10}$, —S(O)$_n$R$^{11}$, —C(O)R$^{12}$, alkyl, cycloalkyl, heterocycloalkyl, aryl, and heteroaryl, each of which is optionally substituted;

n and q are each independently 0, 1, or 2 in each instance;

$R^{20}$ is hydrogen;

$R^8$ is in each instance independently selected from the group consisting of hydrogen, —C(O)R$^{13}$, —S(O)$_2$R$^{14}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^9$ is in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{10}$ is in each instance independently selected from the group consisting of —C(O)R$^{13}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{11}$ is in each instance independently selected from the group consisting of hydrogen, alkyl, cycloalkyl, cycloalkyl-alkyl, heterocycloalkyl, hetoercycloalkyl-alkyl, aryl, arylalkyl, heteroaryl, and heteroarylalkyl, each of which is optionally substituted, when n is 0; $R^{11}$ is in each instance independently selected from the group consisting of alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 1; and $R^{11}$ is in each instance independently selected from the group consisting of —N(R$^{15}$)R$^{16}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted, when n is 2;

$R^{12}$ and $R^{13}$ are each independently selected from the group consisting of hydrogen, —OR$^{19}$, —N(R$^{18}$)R$^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted;

$R^{14}$ is in each instance independently selected from the group consisting of hydrogen, N(R$^{18}$)R$^{19}$, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted; and $R^{15}$, $R^{16}$, $R^{17}$, $R^{18}$, and $R^{19}$ are in each instance independently selected from the group consisting of hydrogen, alkyl, cycloalkyl, cycloalkyl-alkyl, heterocycloalkyl, heterocycloalkyl-alkyl, aryl, arylalkyl, heteroaryl, and heteroarylalkyl, each of which is optionally substituted.

2. The compound of claim 1, wherein $R^{1A}$ and $X^{1A}$ together with the attached nitrogen form an optionally substituted heterocycle.

3. The compound of claim 1, wherein $R^3$ is $C_3$-$C_{10}$ alkyl or cycloalkyl.

4. The compound of claim 1, wherein R is an optionally substituted heteroaryl.

5. The compound of claim 1, wherein $R^5$ is optionally substituted aryl.

6. The compound of claim 1 wherein $X^4$ is $SO_2$; and $R^4$ is optionally substituted aryl.

7. The compound of claim 1, wherein $R^3$ is branched alkyl.

8. The compound of claim 1, wherein $X^5$ is optionally substituted alkylene; and $R^5$ is optionally substituted aryl.

9. The compound of claim 1 wherein R, $R^{1A}$ and $X^{1A}$ and the attached nitrogen are taken together to form an optionally substituted heterocycle.

10. A pharmaceutical composition comprising a compound of claim 1; and one or more pharmaceutically acceptable carriers, diluents, or excipients, or a combination thereof.

11. The compound of claim 1, which is:

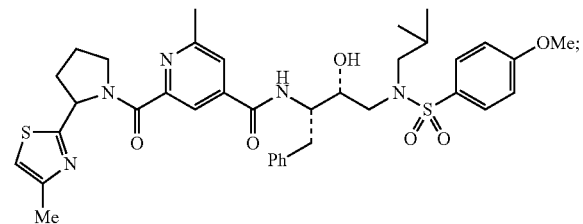

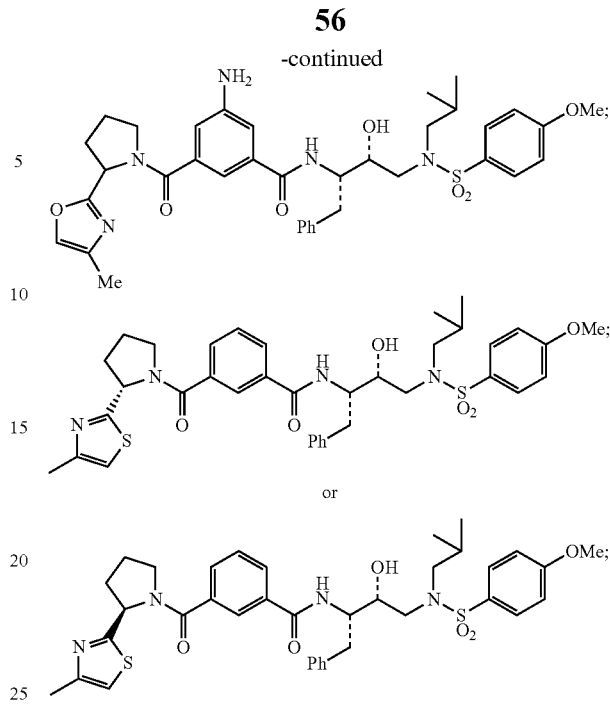

or a pharmaceutically acceptable salt thereof.

* * * * *